(12) United States Patent
Uda et al.

(10) Patent No.: US 9,339,581 B2
(45) Date of Patent: May 17, 2016

(54) ABSORBENT AND ABSORBENT ARTICLE PROVIDED THEREWITH

(71) Applicant: UNICHARM CORPORATION, Shikokuchuo-shi, Ehime (JP)

(72) Inventors: Masashi Uda, Kanonji (JP); Takashi Maruyama, Kanonji (JP); Kenji Oba, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/389,232

(22) PCT Filed: Mar. 25, 2013

(86) PCT No.: PCT/JP2013/058642
§ 371 (c)(1),
(2) Date: Sep. 29, 2014

(87) PCT Pub. No.: WO2013/146711
PCT Pub. Date: Oct. 3, 2013

(65) Prior Publication Data
US 2015/0297781 A1 Oct. 22, 2015

(30) Foreign Application Priority Data
Mar. 30, 2012 (JP) ................................ 2012-082607

(51) Int. Cl.
*A61F 13/20* (2006.01)
*A61L 15/28* (2006.01)
(Continued)

(52) U.S. Cl.
CPC .............. *A61L 15/28* (2013.01); *A61F 13/533* (2013.01); *A61F 13/539* (2013.01); *A61L 15/20* (2013.01);
(Continued)

(58) Field of Classification Search
CPC .................... A61F 13/51113; A61F 13/51104; A61F 13/51059; A61F 13/51061; A61F 13/51066

USPC ............. 604/378, 379, 380, 385.01, 385.101, 604/367
See application file for complete search history.

(56) References Cited

U.S. PATENT DOCUMENTS 5,006,394 A * 4/1991 Baird .................. A61F 13/51
428/138
5,693,037 A * 12/1997 Lee ..................... A61F 13/512
604/378

(Continued)

FOREIGN PATENT DOCUMENTS

EP   1250940 A1   10/2002
EP   1371379 A1   12/2003
(Continued)

*Primary Examiner* — Jacqueline Stephens
(74) *Attorney, Agent, or Firm* — Hauptman Ham, LLP

(57) ABSTRACT

The present invention addresses the problem of providing a novel absorbent that comprises a water-absorbing cellulose-based fiber and a thermoplastic resin fiber, said thermoplastic resin fiber containing as a monomer component an unsaturated carboxylic acid or an unsaturated carboxylic acid anhydride, and has both a sufficient strength and a sufficient absorption property. The absorbent comprises a water-absorbing cellulose-based fiber and a thermoplastic resin fiber, said thermoplastic resin fiber containing as a monomer component an unsaturated carboxylic acid or an unsaturated carboxylic acid anhydride, wherein the mass ratio (the content of the water-absorbing cellulose-based fiber: the content of the thermoplastic resin fiber) is controlled to 90:10 to 50:50 and the density of the absorbent is controlled to 0.06 to 0.14 g/cm³.

13 Claims, 10 Drawing Sheets

(51) Int. Cl.
  *A61F 13/533* (2006.01)
  *A61L 15/56* (2006.01)
  *A61L 15/60* (2006.01)
  *A61L 15/20* (2006.01)
  *A61L 15/42* (2006.01)
  *A61F 13/511* (2006.01)
  *A61F 13/51* (2006.01)
  *A61F 13/53* (2006.01)
  *A61F 13/539* (2006.01)

(52) U.S. Cl.
  CPC .............. *A61L 15/42* (2013.01); *A61L 15/56* (2013.01); *A61L 15/60* (2013.01); *A61F 13/51104* (2013.01); *A61F 13/51113* (2013.01); *A61F 13/52* (2013.01); *A61F 2013/51059* (2013.01); *A61F 2013/530007* (2013.01); *A61F 2013/530036* (2013.01); *A61F 2013/5395* (2013.01)

(56) References Cited

U.S. PATENT DOCUMENTS

| | | | |
|---|---|---|---|
| 6,258,996 B1 * | 7/2001 | Goldman | A61L 15/60 604/358 |
| 2007/0298213 A1 | 12/2007 | Noda et al. | |
| 2007/0298214 A1 | 12/2007 | Noda et al. | |
| 2007/0298220 A1 | 12/2007 | Noda et al. | |
| 2007/0298667 A1 | 12/2007 | Noda et al. | |
| 2007/0298671 A1 | 12/2007 | Noda et al. | |
| 2007/0299416 A1 | 12/2007 | Noda et al. | |
| 2008/0044622 A1 | 2/2008 | Noda et al. | |
| 2008/0044628 A1 | 2/2008 | Noda et al. | |
| 2008/0045915 A1 | 2/2008 | Noda et al. | |
| 2008/0085399 A1 | 4/2008 | Noda et al. | |
| 2009/0282660 A1 | 11/2009 | Noda et al. | |
| 2010/0057030 A1 | 3/2010 | Yang et al. | |
| 2012/0231946 A1 | 9/2012 | Goda et al. | |

FOREIGN PATENT DOCUMENTS

| | | |
|---|---|---|
| EP | 1417946 A1 | 5/2004 |
| JP | 2000512886 A | 10/2000 |
| JP | 2001518986 A | 10/2001 |
| JP | 2004159786 A | 6/2004 |
| JP | 2004230127 A | 8/2004 |
| JP | 2004270041 A | 9/2004 |
| JP | 200823311 A | 2/2008 |
| JP | 2008142424 A | 6/2008 |
| JP | 4221849 B2 | 2/2009 |
| JP | 2010518918 A | 6/2010 |
| JP | 2011117088 A | 6/2011 |
| JP | 5122007 B1 | 1/2013 |
| WO | 9845519 A1 | 10/1998 |
| WO | 9855158 A2 | 12/1998 |
| WO | 2008101163 A2 | 8/2008 |
| WO | 2012133724 A1 | 10/2012 |

* cited by examiner (a)

(b)

200 μm (a)

50 μm (b)

50 μm

ABSORBENT AND ABSORBENT ARTICLE PROVIDED THEREWITH

CROSS-REFERENCES TO RELATED APPLICATIONS

The present application is National Phase of International Application Number PCT/JP2013/058642 filed Mar. 25, 2013 and claims the priority of Japanese patent Application No. 2012-082607 filed Mar. 30, 2012.

1. Technical Field

The present invention relates to an absorbent body and to an absorbent article comprising it.

2. Background Art

The known absorbent bodies for absorbent articles include an absorbent body that comprises hydrophilic fibers (for example, pulp) and synthetic resin fibers crimped into a coil shape (for example, latent crimping eccentric core-sheath composite fibers crimped and contracted into a coil shape by heating), and if necessary superabsorbent polymer particles (PTL 1), and an absorbent body comprising a liquid-absorbing mixture that includes superabsorbent polymer particles and fluff pulp, and a nonwoven fabric formed of filaments of a thermoplastic resin (for example, core-sheath composite fibers having as the sheath a thermoplastic resin selected from polyethylene and ethylene copolymers, and as the core a thermoplastic resin with a higher melting point than the thermoplastic resin forming the sheath) (PTL 2).

There are also known, as thermal bonding composite fibers for airlaid nonwoven fabrics, core-sheath composite fibers that have as the sheath component a modified polyolefin graft-polymerized with a vinyl monomer comprising an unsaturated carboxylic acid or unsaturated carboxylic acid anhydride, and as the core component a resin with a higher melting point than the modified polyolefin (PTLs 3 and 4).

CITATION LIST

Patent Literature

[PTL 1] Japanese Unexamined Patent Publication No. 2004-159786
[PTL 2] Japanese Unexamined Patent Publication No. 2008-142424
[PTL 3] Japanese Patent Publication No. 4221849
[PTL 4] Japanese Unexamined Patent Publication No. 2004-270041

DISCLOSURE OF THE INVENTION

Technical Problem

The absorbent bodies described in PTLs 1 and 2 are designed to prevent deformation and improve cushioning properties, but novel absorbent bodies are desired that have sufficient absorption properties while maintaining sufficient strength even after absorption.

The core-sheath composite fibers described in PTLs 3 and 4 are known to have satisfactory adhesion with cellulose-based fibers, but their suitability for use as constituent components for absorbent bodies has not been known.

It is therefore an object of the present invention to provide a novel absorbent body comprising cellulose-based water-absorbent fibers and thermoplastic resin fibers that comprise an unsaturated carboxylic acid, an unsaturated carboxylic acid anhydride or a mixture thereof as a monomer component, the absorbent body having sufficient absorption properties while maintaining sufficient strength even after absorption, and also to provide an absorbent article comprising the absorbent body.

Solution to Problem

In order to solve the problems described above, the invention provides an absorbent body comprising cellulose-based water-absorbent fibers, and thermoplastic resin fibers that comprise an unsaturated carboxylic acid, an unsaturated carboxylic acid anhydride or a mixture thereof as a monomer component, wherein: a mass ratio of the water-absorbent fibers to the thermoplastic resin fibers in the absorbent body is 90:10 to 50:50; and a density of the absorbent body is 0.06 to 0.14 g/cm$^3$, and also to provide an absorbent article comprising a liquid-permeable layer, a liquid-impermeable layer and an absorbent body of the invention provided between the liquid-permeable layer and the liquid-impermeable layer.

Effect of the Invention

According to the invention there is provided a novel absorbent body comprising cellulose-based water-absorbent fibers, and thermoplastic resin fibers that comprise an unsaturated carboxylic acid, an unsaturated carboxylic acid anhydride or a mixture thereof as the monomer component, the absorbent body having sufficient absorption properties while maintaining sufficient strength even after absorption, as well as an absorbent article comprising the absorbent body.

DESCRIPTION OF EMBODIMENTS

Figure 1:
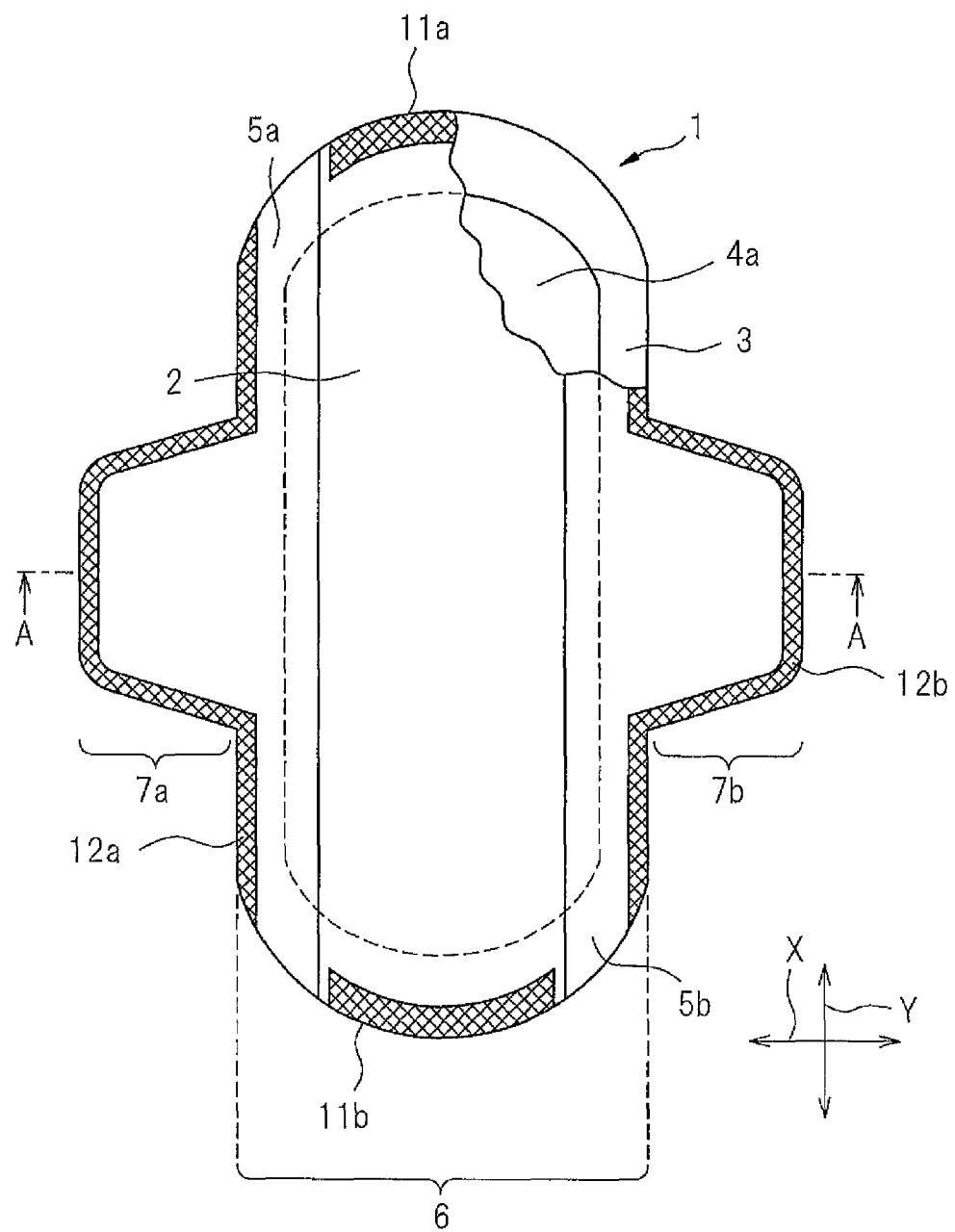
FIG. 1 is a partially broken plan view of a sanitary napkin according to a first embodiment of the invention.

The absorbent body and absorbent article of the invention will now be described.

The absorbent body of the invention comprises cellulose-based water-absorbent fibers (hereunder also abbreviated as "water-absorbent fibers"), and thermoplastic resin fibers that comprise an unsaturated carboxylic acid, an unsaturated carboxylic acid anhydride or a mixture thereof as a monomer component (hereunder also abbreviated as "thermoplastic resin fibers").

The mass ratio of the water-absorbent fibers to the thermoplastic resin fibers in the absorbent body of the invention (water-absorbent fiber content: thermoplastic resin fiber content) is 90:10 to 50:50, and the density of the absorbent body is 0.06 to 0.14 g/cm$^3$. These conditions are the necessary conditions for the absorbent body of the invention to have sufficient absorption properties while maintaining sufficient strength even after absorption.

The density of the absorbent body of the invention is calculated by the following formula:

$$D(g/cm^3) = B(g/m^2)/T(mm) \times 10^{-3}$$

wherein D, B and T represent the density, basis weight and thickness of the absorbent body of the invention, respectively.

The basis weight (g/m$^2$) of the absorbent body of the invention is measured in the following manner:

Three sample pieces each having a size of 100 mm×100 mm are cut out of an absorbent body. Under standard conditions (temperature: 23±2° C., relative humidity: 50±5%), the mass of each sample piece is measured using a direct-reading balance (e.g., Electronic Balance HF-300 manufactured by Kensei Co., Ltd). The mass per unit area (g/m$^2$) of the absorbent body, which is calculated based on an average of the three measured values, corresponds to the basis weight of the absorbent body.

In the measurement of the basis weight of the absorbent body, measurement conditions other than those specified above are selected in accordance with ISO 9073-1 or JIS L 1913 6.2.

The thickness (mm) of the absorbent body of the invention is measured in the following manner:

Under standard conditions (temperature: 23±2° C., relative humidity: 50±5%), a constant pressure of 3 g/cm$^2$ is applied by a thickness gauge (e.g., Thickness Gauge FS-60DS manufactured by DAIEI KAGAKU SEIKI MFG. Co., Ltd, which has a measuring plane of 44 mm in diameter) to five different regions of an absorbent body (If Thickness Gauge FS-60DS is used, the diameter of each region will be 44 mm). At 10 seconds after the pressurization, the thickness of each region is measured by the thickness gauge. The thickness of the absorbent body is calculated as an average of the five measured values.

The density of the absorbent body of the invention can be adjusted to a prescribed range by, for example, increasing the density of a mixed material comprising the water-absorbent fibers and the thermoplastic resin fibers. In order to maintain a fixed range for the density of the absorbent body, it is necessary to minimize elastic recovery of the fibers and maintain a fixed range for the bulk of the absorbent body. In this regard, the absorbent body of the invention allows hydrogen bonds (for example, hydrogen bonds formed between the water-absorbent fibers, between the thermoplastic resin fibers and between the water-absorbent fibers and the thermoplastic resin fibers) to contribute to maintaining the bulk of the absorbent body. Since the hydrogen bonds are broken by liquid absorbed into the absorbent body, they do not inhibit swelling of absorbent materials contained in the absorbent body (the water-absorbent fibers as an essential component, and a superabsorbent material as an optional component).

In a preferred aspect of the absorbent body of the invention (Aspect 1A), the fibers in the absorbent body are bonded together. According to Aspect 1A, bonding between the fibers in the absorbent body improves the strength of the absorbent body (especially the wet strength after liquid absorption). The manner of bonding may be, for example, bonding between the thermoplastic resin fibers or between the thermoplastic resin fibers and the water-absorbent fibers, which is formed by thermal fusion bonding of the thermoplastic resin fibers, or bonding between the thermoplastic resin fibers, between the water-absorbent fibers or between the thermoplastic resin fibers and the water-absorbent fibers, which is formed by hydrogen bonding. When the absorbent body includes other fibers, the thermoplastic resin fibers and/or the water-absorbent fibers may be bonded with the other fibers.

In a preferred aspect of the absorbent body of the invention (Aspect 2A), the absorbent body is obtained by injecting high-pressure steam onto a mixed material comprising the cellulose-based water-absorbent fibers and the thermoplastic resin fibers, to increase a density of the mixed material. According to Aspect 2A, the density of the absorbent body is adjusted to within a desired range by increasing the density, utilizing high-pressure steam injecting. When high-pressure steam is injected onto a mixed material, water vapor permeates into the mixed material, and the hydrogen bonds (for example, the hydrogen bonds formed between the water-absorbent fibers, between the thermoplastic resin fibers and between the water-absorbent fibers and the thermoplastic resin fibers) are broken, thereby softening the mixed material. Thus, less pressure is required to increase the density, and the softened mixed material can be more easily adjusted in density. When the density-adjusted mixed material is dried to reform the hydrogen bonds, elastic recovery (increase in bulk) of the fibers is inhibited, and the density of the absorbent body is kept within a fixed range.

Aspect 2A is particularly suitable when the thermoplastic resin fibers include an unsaturated carboxylic acid anhydride (for example, maleic anhydride or its derivative) as a monomer component. When an unsaturated carboxylic acid anhydride function contained in the thermoplastic resin fibers reacts with water vapor to produce an unsaturated carboxylic acid function, the number of oxygen atoms that can form hydrogen bonds increases, and therefore elastic recovery (increase in bulk) of the density-increased fibers is effectively inhibited.

In a preferred aspect of Aspect 2A (Aspect 3A), a temperature of the high-pressure steam is below a melting point of the thermoplastic resin fibers. According to Aspect 3A, adjustment of the density of the absorbent body is facilitated.

In a preferred aspect of Aspect 2A or 3A (Aspect 4A), a basis weight of the absorbent body is 40 to 900 g/m$^2$. If the basis weight is less than 40 g/m$^2$, an amount of fibers may be too low making it difficult to adjust the density by injecting of high-pressure steam, while if it is greater than 900 g/m$^2$, an amount of fibers may be too great making it difficult for water vapor to permeate to the interior.

In a preferred aspect of the absorbent body of the invention (Aspect 5A), the thermoplastic resin fibers are core-sheath composite fibers having as a sheath component a modified polyolefin graft-polymerized with a vinyl monomer comprising an unsaturated carboxylic acid, an unsaturated carboxylic acid anhydride or a mixture thereof, or a polymer blend of the modified polyolefin and another resin, and as a core component a resin with a higher melting point than the modified polyolefin. In a preferred aspect of the absorbent body of the invention (Aspect 6A), the unsaturated carboxylic acid, unsaturated carboxylic acid anhydride or mixture thereof is maleic acid or its derivative, maleic anhydride or its derivative, or a mixture thereof.

In a preferred aspect of the absorbent body of the invention (Aspect 7 A), a difference between a dry maximum tensile strength and a wet maximum tensile strength is 1 to 5 N/25 mm.

In a preferred aspect of the absorbent body of the invention (Aspect 8 A), the absorbent body comprises a superabsorbent material. According to Aspect 8A, the liquid absorption property of the absorbent body is improved. Since hydrogen bonds are broken by liquid absorbed into the absorbent body, swelling of the superabsorbent material in the absorbent body is not inhibited.

In a preferred aspect of the absorbent body of the invention (Aspect 9A), the absorbent body is colored. According to Aspect 9A, it is easy to visually confirm whether or not the water-absorbent fibers and the thermoplastic resin fibers are evenly dispersed. The color of the absorbed liquid may also be masked. For example, coloration may be blue when the liquid to be absorbed is urine or it may be green when it is menstrual blood, thereby providing the user with a more hygienic feel.

Two or more of Aspects 1A to 9A may also be combined for the absorbent body of the invention.

The absorbent article of the invention comprises a liquid-permeable layer, a liquid-impermeable layer, and an absorbent body of the invention formed between the liquid-permeable layer and the liquid-impermeable layer.

In a preferred aspect of the absorbent article of the invention (Aspect 1B), the absorbent article has a ridge-furrow structure formed on a surface of the liquid-permeable layer side of the absorbent body and/or the surface of the liquid-impermeable layer side of the absorbent body. According to Aspect 1B, the spaces of the furrows are maintained even when force is applied to the absorbent article causing the ridges to collapse, so that the liquid absorption and retention properties of the absorbent body are maintained. Moreover, because of the low contact area between the absorbent body and the liquid-permeable layer, liquid that has been absorbed and retained in the absorbent body does not easily flow back even when force has been applied to the absorbent article, and leakage of liquid from the liquid-permeable layer can be prevented.

In a preferred aspect of the absorbent article of the invention (Aspect 2B), the ridge-furrow structure formed on the surface of the liquid-permeable layer side extends in the lengthwise direction of the absorbent article, while the ridge-furrow structure formed on the surface of the liquid-impermeable layer side extends in the widthwise direction of the absorbent article.

In a preferred aspect of the absorbent article of the invention (Aspect 3B), a fiber density of the absorbent body increases from the surface of the liquid-permeable layer side toward the surface of the liquid-impermeable layer side. According to Aspect 3B, the spot property is high on the liquid-permeable layer side of the absorbent body while the diffusibility is high on the liquid-impermeable layer side of the absorbent body, and therefore the absorbent body has improved liquid permeability and retention, and leakage of the liquid can be prevented.

In a preferred aspect of the absorbent article of the invention (Aspect 4B), the liquid-permeable layer comprises a blood modifying agent with an IOB of 0.00-0.60, a melting point of 45° C. or less, and a water solubility of 0.00-0.05 g in 100 g of water at 25° C. According to Aspect 4B, when a menstrual blood is a liquid to be absorbed by the absorbent article, the blood modifying agent has contact with a menstrual blood that has been discharged onto the liquid-permeable layer, and makes property modification of the menstrual blood. This helps prevent residue of highly viscous menstrual blood into the liquid-permeable layer, reduces stickiness of the liquid-permeable layer, and improves the surface drying property of the liquid-permeable layer, while also leaving less of a visually unpleasant image for the wearer.

In a preferred aspect of Aspect 4B (Aspect 5B), the blood modifying agent is selected from the group consisting of following items (i)-(iii) and combinations thereof:
(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituted for a hydrogen of the hydrocarbon moiety;
with the proviso that when 2 or more oxy groups are inserted in the compound of (ii) or (iii), the oxy groups are not adjacent.

In a preferred aspect of Aspect 4B or 5B (Aspect 6B), the blood modifying agent is selected from the group consisting of following items (i')-(iii') and combinations thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituted for a hydrogen on the hydrocarbon moiety;
with the proviso that when 2 or more same or different bonds are inserted in a compound of (ii') or (iii'), the bonds are not adjacent.

In a preferred aspect of Aspects 4B to 6B (Aspect 7B), the blood modifying agent is selected from the group consisting of following items (A)-(F) and combinations thereof:
(A) an ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety;
(B) an ether of (B1) a compound having a chain hydrocarbon moiety and 2-4 hydroxyl groups substituted for hydrogens on the chain hydrocarbon moiety, and (B2) a compound having a chain hydrocarbon moiety and 1 hydroxyl group substituted for a hydrogen on the chain hydrocarbon moiety;
(C) an ester of (C1) a carboxylic acid, hydroxy acid, alkoxy acid or oxoacid comprising a chain hydrocarbon moiety and 2-4 carboxyl groups substituted for hydrogens on the chain hydrocarbon moiety, and (C2) a compound having a chain hydrocarbon moiety and 1 hydroxyl group substituted for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_2$-$C_6$ alkylene glycol, or its ester or ether; and (F) a chain hydrocarbon.

In a preferred aspect of Aspects 4B to 7B (Aspect 8B), the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_2$-$C_6$ alkylene glycol, ($e_2$) an ester of a polyoxy $C_2$-$C_6$ alkylene glycols and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycols and a chain hydrocarbon tetracarboxylic acid, chain hydrocarbon tricarboxylic acid or chain hydrocarbon dicarboxylic acid, ($e_5$) an ether of a polyoxy $C_2$-$C_6$ alkylene glycol and a chain hydrocarbon tetraol, chain hydrocarbon triol or chain hydrocarbon diol, and ($f_1$) a chain alkane, and combinations thereof.

Two or more of Aspects 1B to 8B may also be combined for the absorbent article of the invention.

There are no particular restrictions on the type and usage of the absorbent article of the invention. For example, absorbent articles include sanitary products and sanitary articles such as sanitary napkins, disposable diapers, panty liners, incontinence pads and perspiration sheets, which may be for humans or animals other than humans, such as pets. There are no particular restrictions on the liquid to be absorbed by the absorbent article, and for example, it may be liquid excreta or body fluid of the user.

Embodiments of the absorbent article of the invention will now be described, using a sanitary napkin as an example.

<First Embodiment>

Figure 2:
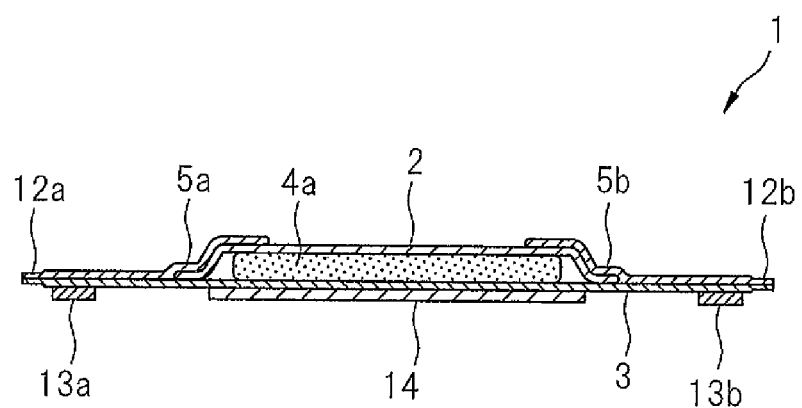
FIG. 2 is a cross-sectional view of FIG. 1 along line A-A.

As shown in FIG. 1 and FIG. 2, the sanitary napkin 1 according to the first embodiment comprises a liquid-permeable top sheet 2, a liquid-impermeable back sheet 3, an absorbent body 4a formed between the top sheet 2 and the back sheet 3, and a pair of side sheets 5a, 5b. In FIG. 1, the X-axial direction is the widthwise direction of the sanitary napkin 1, the Y-axial direction is the lengthwise direction of the sanitary napkin 1, and the direction of the plane extending in the X-axial and Y-axial directions corresponds to the planar direction of the sanitary napkin 1. The same applies to the other drawings as well.

As shown in FIG. 1 and FIG. 2, the edges of the top sheet 2 and the back sheet 3 in the lengthwise direction are bonded by seal sections 11a, 11b, forming a body section 6. The shape of the body section 6 is not particularly restricted so long as it conforms to the female body and underwear, and it may be roughly rectangular, roughly elliptical or roughly gourd-shaped, for example. The dimensions of extension in the lengthwise direction of the outer shape of the body section 6 are preferably 100 to 500 mm and more preferably 150 to 350 mm. The dimensions of extension in the widthwise direction of the outer shape of the body section 6 are preferably 30 to 200 mm and more preferably 40 to 180 mm.

As shown in FIG. 1 and FIG. 2, the pair of side sheets 5a, 5b are provided on both sides in the widthwise direction of the top sheet 2, and the back sheet 3 and side sheets 5a, 5b have the widthwise direction edges bonded together by seal sections 12a, 12b, forming roughly rectangular wing sections 7a, 7b extending from the body section 6 in the widthwise direction. The side sheets 5a, 5b are preferably hydrophobic and water-repellent, so that they can prevent leakage of liquid excreta out in the widthwise direction of the sanitary napkin 1. The material composing the side sheets 5a, 5b may be, for example, a spunbond nonwoven fabric, SMS nonwoven fabric or air-through nonwoven fabric.

As shown in FIG. 2, adhesive sections 13a, 13b are provided on the clothing side of the back sheet 3 forming the wing sections 7a, 7b, and an adhesive section 14 is provided on the clothing side of the back sheet 3 forming the body section 6. The adhesive section 14 is attached to the crotch section of underwear, while the wing sections 7a, 7b are folded toward the outer wall of the underwear and the adhesive sections 13a, 13b are attached to the crotch section of the underwear, thereby stably anchoring the sanitary napkin 1 to the underwear.

Examples of pressure-sensitive adhesives to be used in the adhesive sections 13a, 13b, 14 include styrene-based polymers such as styrene-ethylene-butylene-styrene block copolymer, styrene-butylene polymer, styrene-butylene-styrene block copolymer and styrene-isobutylene-styrene copolymer; tackifiers such as C5 petroleum resins, C9 petroleum resins, dicyclopentadiene-based petroleum resins, rosin-based petroleum resins, polyterpene resins and terpenephenol resins; monomer plasticizers such as tricresyl phosphate, dibutyl phthalate and dioctyl phthalate, and polymer plasticizers such as vinyl polymer and polyester.

The seal sections 11a, 11b, 12a, 12b are provided on the perimeter of the sanitary napkin 1, and examples of bonding methods by the seal sections include embossing, ultrasonic waves and hot-melt adhesives. In order to increase the bonding strength, two or more different bonding methods may be combined (for example, bonding with a hot-melt adhesive followed by embossing).

As an example of embossing, the top sheet 2 and back sheet 3, or the top sheet 2, back sheet 3 and side sheets 5a, 5b, may be passed together between a patterned embossing roll and a flat roll, for embossing of the perimeter section of the absorbent body 4a (a method known as round sealing). By heating the embossing roll and/or flat roll by this method, each sheet is softened so that the seal sections become more distinct. Examples of emboss patterns include lattice-like patterns, zigzag patterns and wavy patterns. In order to impede bending of the sanitary napkin 1 at the borders of the seal sections, the emboss pattern is preferably intermittently elongated.

Examples of hot-melt adhesives include pressure-sensitive adhesives and heat-sensitive adhesives composed mainly of rubber-based compounds such as styrene-ethylene-butadiene-styrene (SEGS), styrene-butadiene-styrene (SBS) or styrene-isoprene-styrene (SIS), or composed mainly of olefin-based compounds such as linear low-density polyethylene; and water-sensitive adhesives comprising water-soluble polymers (such as polyvinyl alcohol, carboxylmethyl cellulose and gelatin or water-swelling polymers (such as polyvinyl acetate and sodium polyacrylate). Specific examples of adhesive coating methods include spiral coating application, coater application, curtain coater application and summit-gun coating.

The sanitary napkin 1 is worn by a user to absorb liquid excreta of the user (such as menstrual blood, urine and vaginal discharge). The user wears it in such a manner that the top sheet 2 is on the skin side of the user, and back sheet 3 is located on the side of the clothing (underwear) of the user. The liquid excreta of the user permeates into the absorbent body 4a through the top sheet 2 and is absorbed by the absorbent body 4a. Leakage of liquid excreta that has been absorbed into the absorbent body 4a is prevented by the back sheet 3.

The top sheet 2 is a sheet through which liquid excreta of the user can permeate, and it is provided on the side in contact with the skin of the user, to improve the feel on the skin when the sanitary napkin 1 is worn by the user.

The top sheet 2 is not particularly restricted so long as it allows permeation of liquid excreta of the user. Examples for the top sheet 2 include nonwoven fabrics, woven fabrics, liquid permeation hole-formed synthetic resin films and meshed net-like sheets, with nonwoven fabrics being preferred among these.

Examples of fibers used to form nonwoven fabrics include natural fibers (wool, cotton and the like), regenerated fibers (rayon, acetate and the like), inorganic fibers (glass fibers, carbon fibers and the like), synthetic resin fibers (polyolefins such as polyethylene, polypropylene, polybutylene, ethylene-vinyl acetate copolymer, ethylene-ethyl acrylate copolymer, ethylene-acrylic acid copolymer, and ionomer resins; polyesters such as polyethylene terephthalate, polybutylene terephthalate, polytrimethylene terephthalate and polylactic acid, and polyamides such as nylon). The nonwoven fabric may be combined with composite fibers such as core/sheath fibers, side-by-side fibers and sea/island fibers, hollow type fibers; irregularly shaped fibers such as flat fibers, Y-shaped fibers or C-shaped fibers; solid crimped fibers such as latent crimped or developed crimped fibers, or split fibers that have been split by a physical load such as a water stream, heat, embossing or the like.

Examples for the method of producing a nonwoven fabric include forming a web (fleece) and physically or chemically bonding the fibers together, methods for forming a web include spunbond methods, dry methods (carding methods, spunbond methods, meltblown methods and airlaid methods), and wet methods, and bonding methods include thermal bond methods, chemical bond methods, needle punching methods, stitch bond methods and spunlace methods. Instead of a nonwoven fabric produced as described above, spunlace formed into a sheet by a hydroentangling method may be used as the top sheet 2. There may also be used for the top sheet 2 a nonwoven fabric having irregularities on the skin side (for example, a nonwoven fabric having a lower layer side with heat-shrinkable fibers or the like, which contracts to form irregularities on the upper layer side, or a nonwoven fabric in which irregularities are formed by applying air during web formation). Forming irregularities on the skin side in this manner can reduce the contact area between the top sheet 2 and the skin.

The thickness, basis weight and density of the top sheet 2 can be appropriately adjusted in ranges that allow permeation of liquid excreta of the user. When a nonwoven fabric is used as the top sheet 2, the fineness, length and density of the fibers composing the nonwoven fabric and the basis weight and thickness of the nonwoven fabric may be appropriately adjusted from the viewpoint of permeability of liquid excreta and feel on the skin.

From the viewpoint of increasing the concealing property of the top sheet 2, an inorganic filler such as titanium oxide, barium sulfate or calcium carbonate may be added to the nonwoven fabric used as the top sheet 2. When the nonwoven fabric fibers are core-sheath type composite fibers, the inorganic filler may be added only to the core or only to the sheath.

The back sheet 3 is a sheet that does not allow permeation of liquid excreta of the user, and it is provided on the side in contact with the clothing (underwear) of the user to prevent leakage of liquid excreta that has been absorbed in the absorbent body 4a. The back sheet 3 is preferably moisture-permeable in addition to being liquid-impermeable, in order to reduce mustiness during wear.

The back sheet 3 is not particularly restricted so long as it does not allow permeation of liquid excreta of the user. Examples for the back sheet 3 include waterproof treated nonwoven fabrics, films of synthetic resins (such as polyethylene, polypropylene and polyethylene terephthalate), composite sheets comprising nonwoven fabrics and synthetic resin films (such as composite films having an air permeable synthetic resin film bonded to a spunbond or spunlace nonwoven fabric), and SMS nonwoven fabrics comprising a highly water-resistant meltblown nonwoven fabric sandwiched between high-strength spunbond nonwoven fabrics.

The absorbent body 4a comprises cellulose-based water-absorbent fibers and thermoplastic resin fibers that include an unsaturated carboxylic acid, an unsaturated carboxylic acid anhydride or a mixture thereof as a monomer component, the water-absorbent fibers contributing mainly to liquid absorption and retention of the absorbent body 4a, and the thermoplastic resin fibers contributing mainly to the strength of the absorbent body 4a (especially the wet strength after liquid absorption).

The water-absorbent fibers and the thermoplastic resin fibers are present in the absorbent body 4a in a mixed state. The intersections between the fibers (for example, the intersections between the thermoplastic resin fibers or the intersections between the thermoplastic resin fibers and the water-absorbent fibers) are bonded by thermal fusion bonding of the thermoplastic resin fibers. This improves the strength of the absorbent body 4a (especially the wet strength after liquid absorption). The fibers are also forcefully tangled, and bonded by hydrogen bonds formed between the thermoplastic resin fibers, between the water-absorbent fibers or between the thermoplastic resin fibers and the water-absorbent fibers. When the absorbent body 4a includes other fibers, the thermoplastic resin fibers and/or the water-absorbent fibers may be bonded with the other fibers.

The thermal fusion bonding is accomplished, for example, by heating a mixed material comprising the water-absorbent fibers and the thermoplastic resin fibers at a temperature above the melting point of the thermoplastic resin fibers. The heating temperature may be appropriately adjusted depending on the type of thermoplastic resin fibers. The temperature above the melting point of the thermoplastic resin fibers may be any that is above the temperature at which a portion of the thermoplastic resin fibers melt, and when the thermoplastic resin fibers are core-sheath composite fibers, for example, it may be above the temperature at which the sheath component melts.

The mass ratio of the water-absorbent fibers to the thermoplastic resin fibers in the absorbent body 4a (water-absorbent fiber content: thermoplastic resin fiber content) is between 90:10 and 50:50, and it may be appropriately varied within this range but is preferably between 80:20 and 60:40. If the mass ratio of the thermoplastic resin fibers to the water-absorbent fibers is lower than 10/90, it may not be possible to impart sufficient strength (especially wet strength after liquid absorption) to the absorbent body 4a. If the mass ratio of the thermoplastic resin fibers to the water-absorbent fibers is higher than 50/50, on the other hand, it may not be possible to impart a sufficient liquid absorption property to the absorbent body 4a.

The density of the absorbent body 4a is between 0.06 and 0.14 g/cm$^3$ and it may be appropriately varied within this range, but is preferably between 0.07 and 0.12 g/cm$^3$ and more preferably between 0.08 and 0.1 g/cm$^3$. If the mass ratio of the water-absorbent fibers to the thermoplastic resin fibers in the absorbent body 4a is between 90:10 and 50:50 and the density of the absorbent body 4a is between 0.06 and 0.14 g/cm$^3$, it may be possible to impart a sufficient liquid absorption property to the absorbent body 4a.

The density of the absorbent body 4a is adjusted to the prescribed range by increasing the density of a mixed material comprising the water-absorbent fibers and the thermoplastic resin fibers. In order to maintain a fixed range for the density of the absorbent body 4a, it is necessary to minimize elastic recovery of the fibers and maintain a fixed range for the bulk of the absorbent body 4a. In this regard, hydrogen bonding (for example, hydrogen bonding formed between the water-absorbent fibers, between the thermoplastic resin fibers and between the water-absorbent fibers and the thermoplastic resin fibers) can contribute to maintaining the bulk of the absorbent body 4a. Hydrogen bonds are formed, for example, between the oxygen atoms of the thermoplastic resin fibers (for example, the oxygen atoms of carboxyl groups, acyl groups and ether bonds) and the hydrogens of cellulose (for example, the hydrogen atoms of hydroxyl groups). Since the hydrogen bonds are broken by liquid absorbed into the absorbent body 4a, they do not inhibit swelling of absorbent materials contained in the absorbent body 4a (the water-absorbent fibers as an essential component, and a superabsorbent material as an optional component).

The dry maximum tensile strength of the absorbent body 4a (the maximum tensile strength for a basis weight of 200 g/m$^2$) is preferably between 3 and 36 N/25 mm and more preferably between 8 and 20 N/25 mm, and the wet maximum tensile strength of the absorbent body 4a (the maximum tensile strength for a basis weight of 200 g/m$^2$) is preferably between 2 and 32 N/25 mm and more preferably between 5 and 15 N/25 mm. Here, "N/25 mm" means the maximum tensile strength (N) per 25 mm width in the planar direction of the absorbent body 4a, the planar direction of the absorbent body 4a being, for example, the machine direction (MD direction) during production of the absorbent body 4a or the direction perpendicular to the MD direction (CD direction), but preferably the MD direction.

The dry maximum tensile strength of the absorbent body 4a is measured by mounting a sample piece (150 mm length× 25 mm width) on a tensile tester (AG-1kNI manufactured by Shimadzu Corp.) under standard conditions (temperature: 20° C., humidity: 60%), with a grip spacing of 100 mm, and applying a load (maximum point load) at a pull rate of 100 mm/min until the sample piece is severed. In this case, the "N/25 mm" refers to the maximum tensile strength (N) per 25 mm width in the lengthwise direction of the sample piece.

The wet maximum tensile strength of the absorbent body 4a is measured by dipping a sample piece (150 mm length×25 mm width) in ion-exchanged water until it sinks under its own weight, or immersing the sample piece in water for 1 hour or longer, and then performing measurement in the same manner as for the dry maximum tensile strength (ISO 9073-3, JIS L 1913 6.3). In this case, the "N/25 mm" refers to the maximum tensile strength (N) per 25 mm width in the lengthwise direction of the sample piece.

The difference between the dry maximum tensile strength and the wet maximum tensile strength (dry maximum tensile strength—wet maximum tensile strength) is preferably 1 to 5 N/25 mm and more preferably 2 to 4 N/25 mm. Since the hydrogen bonds formed during dryness are broken when wet, the difference between the dry maximum tensile strength and the wet maximum tensile strength is an indicator of the extent of hydrogen bonding.

Examples of cellulose-based water-absorbent fibers include wood pulp obtained using conifers or broadleaf trees as starting materials (for example, mechanical pulp such as groundwood pulp, refiner ground pulp, thermomechanical pulp and chemithermomechanical pulp; chemical pulp such as Kraft pulp, sulfide pulp and alkaline pulp; and semichemical pulp); mercerized pulp or crosslinked pulp obtained by chemical treatment of wood pulp; nonwood pulp such as bagasse, kenaf, bamboo, hemp and cotton (for example, cotton linter); and regenerated fiber such as rayon fiber.

Thermoplastic resin fibers comprising an unsaturated carboxylic acid, an unsaturated carboxylic acid anhydride or a mixture thereof as a monomer component are not particularly restricted and may be appropriately selected from the viewpoint of strength, hydrogen bonding properties and thermal adhesiveness.

Examples of the thermoplastic resin fibers include core-sheath composite fibers having as a sheath component a modified polyolefin that has been graft-polymerized with a vinyl monomer comprising an unsaturated carboxylic acid, an unsaturated carboxylic acid anhydride or a mixture thereof, or a polymer blend of the modified polyolefin with another resin, and as a core component a resin with a higher melting point than the modified polyolefin.

Examples of unsaturated carboxylic acids or unsaturated carboxylic acid anhydrides include vinyl monomers such as maleic acid and its derivatives, maleic anhydride and its derivatives, fumaric acid and its derivatives, unsaturated derivatives of malonic acid, and unsaturated derivatives of succinic acid, and other vinyl monomers including radical-polymerizing general purpose monomers, for example, styrenes such as styrene and α-methylstyrene; and (meth)acrylic acid esters such as methyl (meth)acrylate, ethyl (meth)acrylate, 2-hydroxyethyl (meth)acrylate and dimethylaminoethyl (meth)acrylate. Examples of maleic acid derivatives and maleic anhydride derivatives include citraconic acid, citraconic acid anhydride and pyrocinchonic acid anhydride, examples of fumaric acid derivatives and malonic acid unsaturated derivatives include 3-butene-1,1-dicarboxylic acid, benzylidenemalonic acid and isopropylidenemalonic acid, and examples of succinic acid unsaturated derivatives include itaconic acid and itaconic acid anhydride.

The trunk polymer of a modified polyolefin may be linear low-density polyethylene (LLDPE), low-density polyethylene (LDPE), medium-density polyethylene (MDPE), high-density polyethylene (HDPE), polypropylene, polybutylene, or a copolymer composed mainly of the foregoing (for example, ethylene-vinyl acetate copolymer (EVA), ethylene-ethyl acrylate copolymer (EEA), ethylene-acrylic acid copolymer (EAA) or an ionomer resin).

Graft polymerization of a vinyl monomer on a trunk polymer may be accomplished by a common method, for example, by a method of using a radical initiator, mixing an unsaturated carboxylic acid or unsaturated carboxylic acid anhydride and a vinyl monomer with a polyolefin and introducing side chains of a random copolymer, or a method of successively polymerizing different monomers and introducing side chains of a block copolymer.

The sheath component may be a modified polyolefin alone, or it may be a polymer blend of a modified polyolefin and another resin. The other resin is preferably a polyolefin, and more preferably the same polyolefin as the trunk polymer of the modified polyolefin. For example, when the trunk polymer is polyethylene the other resin is preferably also polyethylene.

The resin to be used as the core component is not particularly restricted so long as it is a resin with a higher melting point than the modified polyolefin, and for example, it may be a polyamide such as 6-nylon or 6,6-nylon; a polyester of polyethylene terephthalate (PET), polytrimethylene terephthalate (PTT), polybutylene terephthalate (PBT), linear or branched polyhydroxyalkane acid up to C20, such as polylactic acid or polyglycolic acid, or a copolymer composed mainly thereof, or a copolymerized polyester composed mainly of an alkylene terephthalate copolymerized with a small amount of another component. PET is preferred from the viewpoint of its elastic repulsion and high cushioning properties, as well as from an economical viewpoint, since it can be commercially obtained at low cost.

Spinning can be accomplished if the composite ratio of the sheath component to the core component is in the range of 10/90 to 90/10, and preferably 30/70 to 70/30. If the sheath component ratio is excessively reduced the thermal adhesiveness may be lowered, and if it is excessively increased the spinnability may be lowered.

Additives such as antioxidants, light stabilizers, ultraviolet absorbers, neutralizers, nucleating agents, epoxy stabilizers, lubricants, antimicrobial agents, flame retardants, antistatic agents, pigments or plasticizers may also be added to the thermoplastic resin fibers if necessary. The thermoplastic resin fibers are preferably subjected to hydrophilicizing treatment with a surfactant, hydrophilic agent or the like.

The fiber lengths of the thermoplastic resin fibers are not particularly restricted, but they are preferably 3 to 70 mm and more preferably 5 to 20 mm when they are to be mixed with pulp by an airlaid system. Below this range, the number of bonding points with the water-absorbent fibers may be reduced, making it impossible to impart sufficient strength to the absorbent body 4a. Above this range, the defibration property may be notably reduced, generating numerous non-defibrated fibers, and thus resulting in fabric irregularities and reduced uniformity of the absorbent body 4a. The fineness of the thermoplastic resin fibers is preferably 0.5 to 10 dtex and more preferably 1.5 to 5 dtex. If the fineness is less than 0.5 dtex the defibration property may be reduced, and if it is greater than 10 dtex the number of fibers may be reduced, lowering the strength.

A three-dimensional crimped form may also be added to the thermoplastic resin fibers. This will allow the buckling strength of the fibers to act in the thickness direction and inhibit collapse under external pressure, even when the fiber orientation is in the planar direction. The three-dimensional crimped form may be, for example, a zig-zag, Ω or spiral form, and the method of creating the three-dimensional crimped form may be, for example, shaping by machine-texturing or heat shrinkage. Machine-texturing can be controlled by circumferential speed differences in the line speed, and on the heat and pressure, for continuous linear fibers after spinning, and a greater number of crimps per unit length will increase the buckling strength against external pressure. The number of crimps will usually be 5 to 35/inch, and is preferably 15 to 30/inch. For creation of a form by heat shrinkage, for example, heat may be applied to fibers composed of two or more different resins with different melting points, to accomplish three-dimensional crimping utilizing the difference in heat shrinkage produced by the differences in melting points. The fiber cross-sectional shape may be, for example, that of eccentric type or side-by-side type core-sheath composite fibers. The heat shrinkage factor of such fibers is preferably 5-90% and more preferably 10-80%.

The absorbent body 4a preferably comprises a superabsorbent material (such as superabsorbent polymers or superabsorbent fibers) in addition to the water-absorbent fibers and the thermoplastic resin fibers. The content of the superabsorbent material will usually be 5 to 80 mass %, preferably 10 to 60 mass % and more preferably 20 to 40 mass % of the absorbent body 4a. Examples of superabsorbent materials include starch-based, cellulose-based and synthetic polymer superabsorbent materials. Examples of starch-based or cellulose-based superabsorbent materials include starch-acrylic acid (salt) graft copolymer, saponified starch-acrylonitrile copolymer and crosslinked sodium carboxymethyl cellulose, and examples of synthetic polymer-based superabsorbent materials include polyacrylic acid salt-based, polysulfonic acid salt-based, maleic anhydride salt-based, polyacrylamide-based, polyvinyl alcohol-based, polyethylene oxide-based, polyaspartic acid salt-based, polyglutamic acid salt-based, polyalginic acid salt-based, starch-based and cellulose-based superabsorbent polymers (SAP), among which polyacrylic acid salt-based (especially sodium polyacrylate-based) superabsorbent polymers are preferred. Examples of superabsorbent material forms include particulate, filamentous and scaly forms, and in the case of particulates, the particle size is preferably 50 to 1000 μm and more preferably 100 to 600 μm.

In order to impart the desired function to the absorbent body 4a, there may be added silver, copper, zinc, silica, active carbon, aluminosilicate compounds, zeolite, or the like. These can impart functions such as deodorant, antibacterial or heat-absorbing effects.

The absorbent body 4a may be colored with a pigment or the like. This will facilitate visual confirmation of whether or not the water-absorbent fibers and the thermoplastic resin fibers are evenly dispersed. The color of the absorbed liquid may also be masked. For example, coloration may be blue when the liquid to be absorbed is urine or it may be green when it is menstrual blood, thereby providing the user with a more hygienic feel.

The thickness and basis weight of the absorbent body 4a can be appropriately adjusted according to the properties desired for the sanitary napkin 1 (for example, absorption property, strength and lightweight property). The thickness of the absorbent body 4a will usually be 0.1 to 15 mm, preferably 1 to 10 mm and more preferably 2 to 5 mm, and the basis weight will usually be 20 to 1000 $g/m^2$, preferably 50 to 800 $g/m^2$ and more preferably 100 to 500 $g/m^2$. The thickness and basis weight of the absorbent body 4a may be constant across the entire absorbent body 4a, or it may partially differ.

The fiber density of the absorbent body 4a preferably increases from the surface of the top sheet 2 side toward the surface of the back sheet 3 side. Such a fiber density gradient will increase the spot property on the top sheet 2 side of the absorbent body 4a and increase diffusibility on the back sheet 3 side of the absorbent body 4a, thereby allowing the absorbent body 4a to have excellent liquid-permeability and retention and helping to prevent leakage of liquid excreta from the top sheet 2.

The absorbent body 4a may also be integrally formed with the top sheet 2. When the absorbent body 4a is integrally formed with the top sheet 2, separation between the top sheet 2 and the absorbent body 4a is prevented even when force is applied to the sanitary napkin 1 (for example, force during activities such as walking, standing or sitting by the user), and therefore migration of liquid from the top sheet 2 into the absorbent body 4a is supported. This will improve the surface drying property of the top sheet 2 and result in less stickiness and wetness for the user. Examples of integral forming methods include embossing, hot fluid fusion, ultrasonic waves, hot-melt adhesives, and the like.

A second sheet may also be provided between the top sheet 2 and the absorbent body 4a. The second sheet is not particularly restricted so long as it allows permeation of liquid excreta of the user, similar to the top sheet 2. The second sheet may be any of the same examples as for the top sheet 2.

The absorbent body 4a may have a domed section. The domed section is a section that protrudes in the thickness direction of the absorbent body 4a, toward the section that contacts with the excretory opening of the top sheet 2 (when an user wears the sanitary napkin 1, this is the section that contacts with the excretory opening of the user (for example, the labia minora and/or labia majora)). When the absorbent body 4a has a domed section, the domed section fits with the excretory opening of the user (for example, the labia minora and/or labia majora) through the top sheet 2, and therefore leakage of liquid excreta to the exterior of the sanitary napkin 1 is prevented. In order to allow the domed section to fit with the excretory opening of the user (for example, the labia minora and/or labia majora) through the top sheet 2, the top sheet 2 preferably has a shape that follows the domed section of the absorbent body 4a. The basis weight and/or density of the absorbent body 4a may be different at the domed section and at its periphery. For example, the basis weight and/or density of the domed section may be higher or lower than the basis weight and/or density at the periphery. For example, a suction drum may be used to layer the absorbent body material in order to vary the basis weight and/or density, thereby allowing various layering patterns to be created.

The absorbent body 4a may be covered with a covering material. The covering material is not particularly restricted so long as it has liquid-permeable and absorbent body-holding properties, and from the viewpoint of low cost and absorbent body-holding properties, it is preferably a tissue composed mainly of ground pulp and formed by a wet method.

<Second Embodiment>

According to the second embodiment, there is provided between the top sheet 2 and back sheet 3, instead of the absorbent body 4a, an absorbent body 4a' (not shown) obtained by injecting high-pressure steam onto a mixed material comprising the water-absorbent fibers and the thermoplastic resin fibers to increase the density of the mixed material. The construction of the absorbent body 4a' is identical to that of the absorbent body 4a except for the aspect of utilizing injecting of high-pressure steam for density adjustment, and therefore its explanation will be omitted except when necessary.

The density of the absorbent body 4a' is adjusted to within the desired range by increasing the density, utilizing high-pressure steam injecting. When high-pressure steam is injected onto a mixed material, water vapor permeates into the mixed material, and the hydrogen bonds (for example, the hydrogen bonds formed between the water-absorbent fibers, between the thermoplastic resin fibers and between the water-absorbent fibers and the thermoplastic resin fibers) are broken, thereby softening the mixed material. Thus, less pressure is required to increase the density, and the softened mixed material can be more easily adjusted in density. When the density-adjusted mixed material is dried to reform the hydrogen bonds, elastic recovery (increase in bulk) of the fibers is inhibited, and the density of the absorbent body 4a' is kept within a fixed range.

The density increase by injecting of high-pressure steam is particularly suitable when the thermoplastic resin fibers include an unsaturated carboxylic acid anhydride (for example, maleic anhydride or its derivative) as a monomer component. When an unsaturated carboxylic acid anhydride function contained in the thermoplastic resin fibers reacts with water vapor to produce an unsaturated carboxylic acid function, the number of oxygen atoms that can form hydrogen bonds increases, and therefore elastic recovery of the density-modified fibers (increase in bulk) is effectively inhibited.

Density increase by injecting of high-pressure steam is carried out, for example, after the thermoplastic resin fibers have been bonded to the water-absorbent fibers. The temperature and vapor pressure of the high-pressure steam is appropriately adjusted depending on the desired density range. The temperature of the high-pressure steam is preferably lower than the melting point of the thermoplastic resin fibers (for example, the melting point of the sheath component when the thermoplastic resin fibers are core-sheath composite fibers). The high-pressure steam is preferably injected at 0.03 kg/m$^2$ to 1.23 kg/m$^2$ per unit surface area. The vapor pressure of the high-pressure steam will usually be 0.1 to 2 Mpa and is preferably 0.3 to 0.8 Mpa.

The basis weight of the absorbent body 4a' is preferably 40 to 900 g/m$^2$ and more preferably 100 to 400 g/m$^2$. If the basis weight is less than 40 g/m$^2$, the amount of fibers may be too low making it difficult to increase the density by injecting of high-pressure steam, while if it is greater than 900 g/m$^2$, the amount of fibers may be too great making it difficult for water vapor to permeate to the interior.

The surface of the absorbent body 4a' may also have ridges and furrows formed by injecting of high-pressure steam. The number of ridges and furrows and their spacing vary according to the number of nozzles injecting the high-pressure steam, and their pitch. The sections where the high-pressure steam is injected become the furrows.

The high-pressure steam may be injected over the entire mixed material, or only a portion thereof. The temperature and vapor pressure for the injected high-pressure steam may be varied for different sections of the mixed material. By partially injecting the high-pressure steam on the mixed material, or by altering the temperature and vapor pressure of the injected high-pressure steam, it is possible to vary the density distribution of the absorbent body 4a' at different sections of the mixed material.

The high-pressure steam may be injected while pressing the mixed material, or it may be injected without pressing. By injecting the high-pressure steam on a section of the mixed material while pressing and injecting the high-pressure steam on the other sections without pressing, it is possible to vary the density distribution of the absorbent body 4a'. For example, when high-pressure steam is injected on the mixed material while passing through mesh conveyor belts that have partial openings, since the high-pressure steam is directly injected without pressing at the open sections of the mesh conveyor belt, while the high-pressure steam is injected while pressing at the non-open sections of the mesh conveyor belt, it is possible to vary the density distribution.

Density increase by injecting of high-pressure steam is advantageous over other methods in the following aspects. When a mixed material is increased in density by press roll-molding, it must be highly compacted to impart bonding strength between the fibers and overcome repulsion between the fibers. Once compressed by high compaction, the fibers undergo elastic recovery and are restored to their original bulk. On the other hand, when a mixed material is increased in density by combining press rolling with water spraying, a basis weight of 100 g/m² or less will allow moisture to permeate to the interior of the mixed material, whereas a basis weight of greater than 100 g/m² will make it difficult for moisture to permeate to the interior of the mixed material and will not allow formation of hydrogen bonds inside the mixed material. If excess moisture is applied, the moisture will be able to permeate to the interior of the mixed material, but excessive heat and time will be required for the moisture to evaporate off, and thus productivity will be reduced. However, the density is to be increased by injecting of high-pressure steam, water vapor permeates into the mixed material, and the hydrogen bonds (for example, the hydrogen bonds formed between the water-absorbent fibers, between the thermoplastic resin fibers and between the water-absorbent fibers and the thermoplastic resin fibers) are broken, thereby softening the mixed material. Consequently, less pressure is required to increase the density, and the softened mixed material can be more easily adjusted in density. In addition, the water vapor easily evaporates resulting in a shorter drying time, and improving productivity.

<Third Embodiment>

Figure 3:
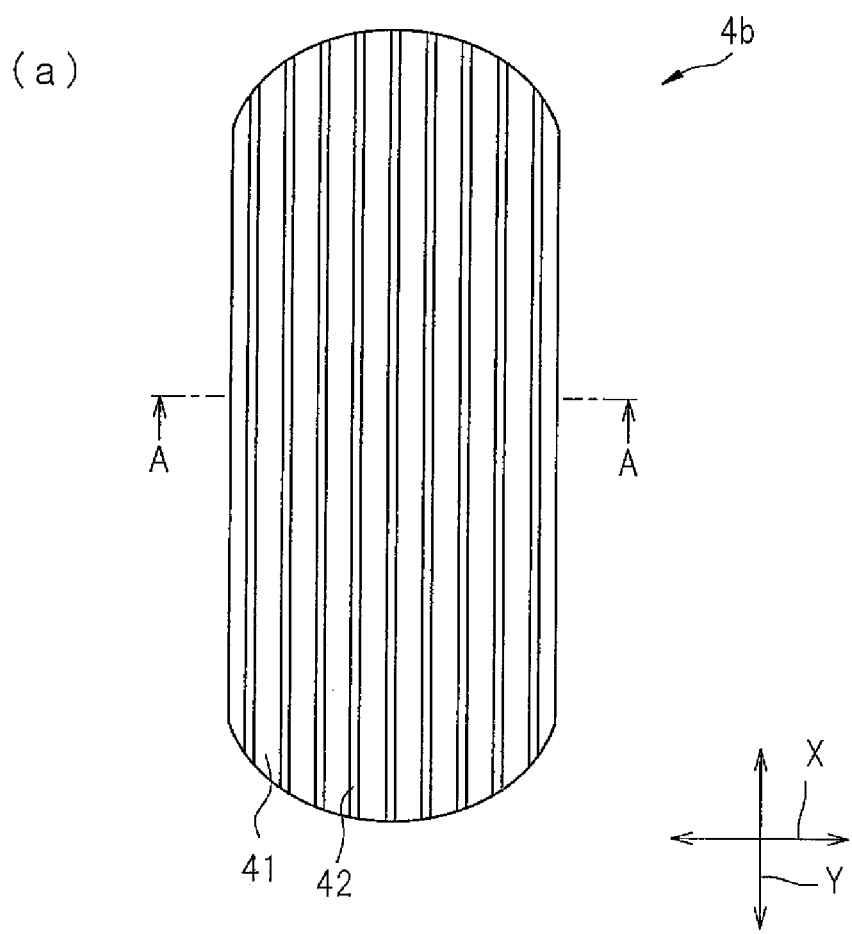
FIG. 3(a) is a top view of an absorbent body to be used in a sanitary napkin according to a second embodiment of the invention (a plan view as seen from the top sheet side)
FIG. 3(b) is a cross-sectional view of FIG. 3(a) along line A-A.
Figure 3:
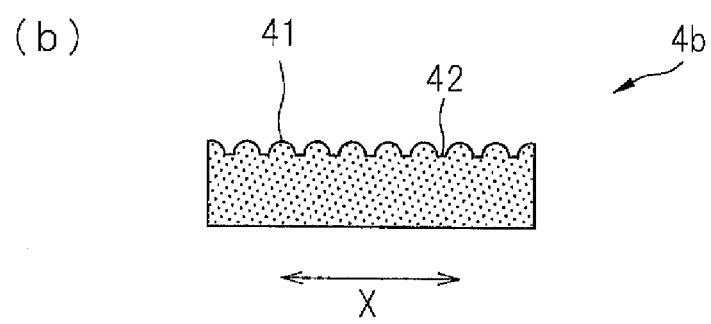
Figure 4:
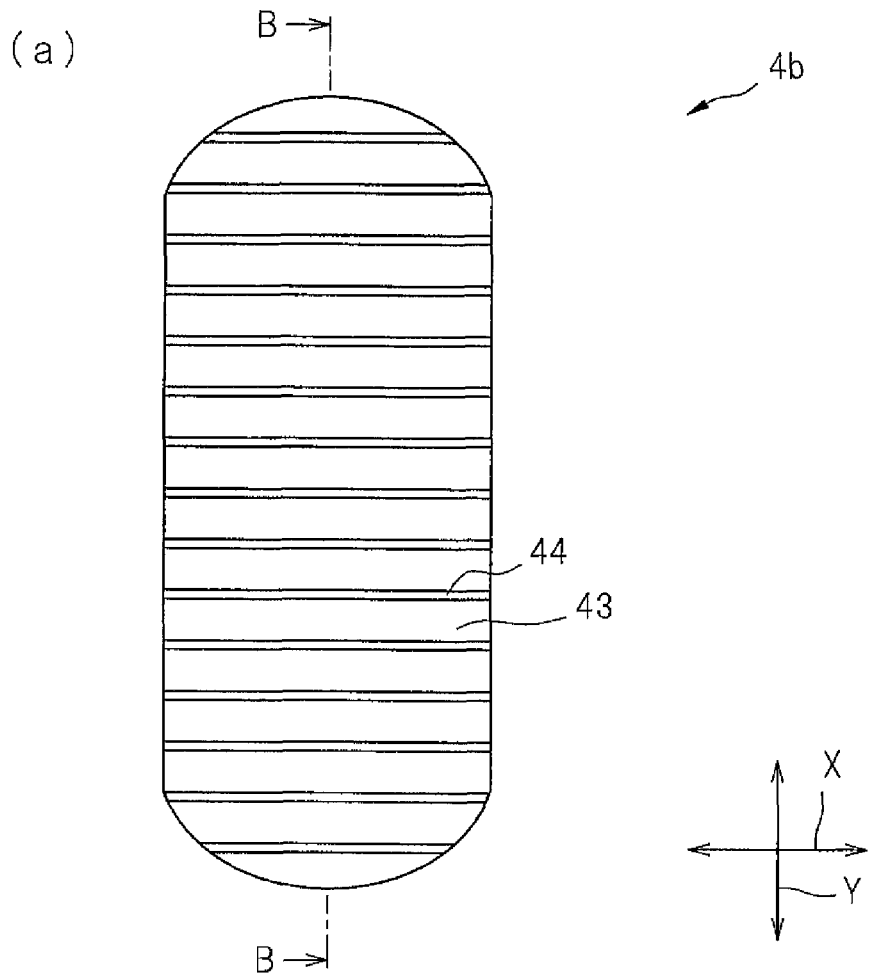
FIG. 4(a) is a bottom view of an absorbent body to be used in a sanitary napkin according to a second embodiment of the invention (a plan view as seen from the back sheet side)
FIG. 4(b) is a cross-sectional view of FIG. 4(a) along line B-B.
Figure 4:
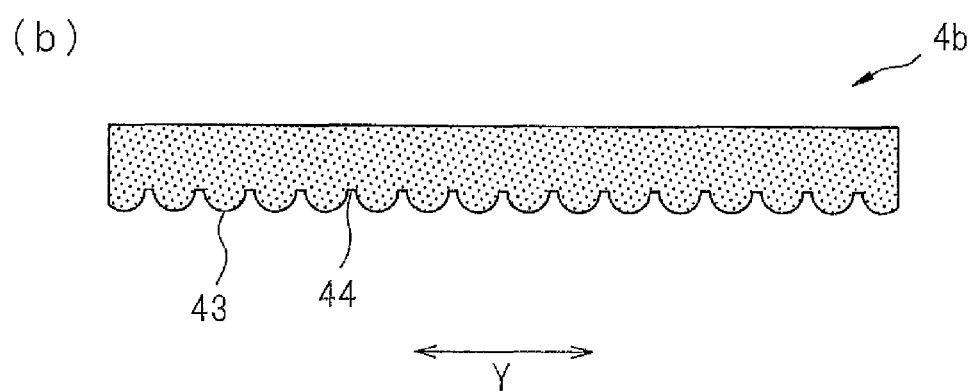

According to the third embodiment, the absorbent body $4b$ shown in FIG. 3 and FIG. 4 is provided instead of the absorbent body $4a$, between the top sheet 2 and the back sheet 3.

As shown in FIG. 3 and FIG. 4, the absorbent body $4b$ is identical to the absorbent body $4a$, differing only by having a plurality of ridges 41 and furrows 42 formed on the surface of the top sheet 2 side, and a plurality of ridges 43 and furrows 44 are formed on the surface of the back sheet 3 side. According to this embodiment, a ridge-furrow structure is formed on both surfaces on the top sheet 2 side and the back sheet 3 side of the absorbent body $4b$, but the ridge-furrow structure may instead be formed only on the surface of the top sheet 2 side. In FIG. 3 and FIG. 4 the boundaries between the ridges 41,43 and the furrows 42,44 are shown as solid lines for convenience, the wide regions being surrounded by two solid lines corresponding to ridges 41,43 and the narrow regions being surrounded by two solid lines corresponding to furrows 42,44.

As shown in FIG. 3, the ridges 41 and furrows 42 extend in the lengthwise direction (Y-axial direction) of the sanitary napkin 1, and are alternately disposed in the widthwise direction (X-axial direction) of the sanitary napkin 1. The ridges 41 and furrows 42 extend continuously in the lengthwise direction (Y-axial direction) of the sanitary napkin 1, but they may also extend intermittently, lacking some sections. For example, the ridges 41 and furrows 42 may extend intermittently so that the missing sections of the ridges 41 and furrows 42 form rectangles or zigzags in a planar view.

As shown in FIG. 4, the ridges 43 and furrows 44 extend in the widthwise direction (X-axial direction) of the sanitary napkin 1, and are alternately disposed in the lengthwise direction (Y-axial direction) of the sanitary napkin 1. The ridges 43 and furrows 44 extend continuously in the widthwise direction (X-axial direction) of the sanitary napkin 1, but they may also extend intermittently, lacking some sections. For example, the ridges 43 or furrows 44 may extend intermittently so that the missing sections of the ridges 43 or furrows 44 form rectangles or zigzags in a planar view. Since a plurality of ridges 43 and furrows 44 are formed on the surface of the back sheet 3 side in the absorbent body $4b$, the absorbent body $4b$ is resistant to slipping even when force is applied in the widthwise direction of the absorbent body $4b$, and the absorbent body $4b$ easily deforms to a curve along the shape of the user's body. It therefore produces less of an uncomfortable feeling for the user.

As shown in FIG. 3 and FIG. 4, the top sections and sides of the ridges 41,43 are curved surfaces, and the cross-sectional shapes of the ridges 41,43 are approximately inverted U-shapes along the top sheet 2 or back sheet 3. The cross-sectional shapes of the ridges 41,43 may be appropriately modified, and for example, they may be dome-shaped, trapezoidal, triangular or Ω-shaped quadrilaterals. The widths of the ridges 41,43 are narrowed from the bottom sections toward the top sections so that the spaces of the furrows 42,44 are maintained even if force is applied to the absorbent body $4b$ causing the ridges 41,43 to collapse.

Figure 5:
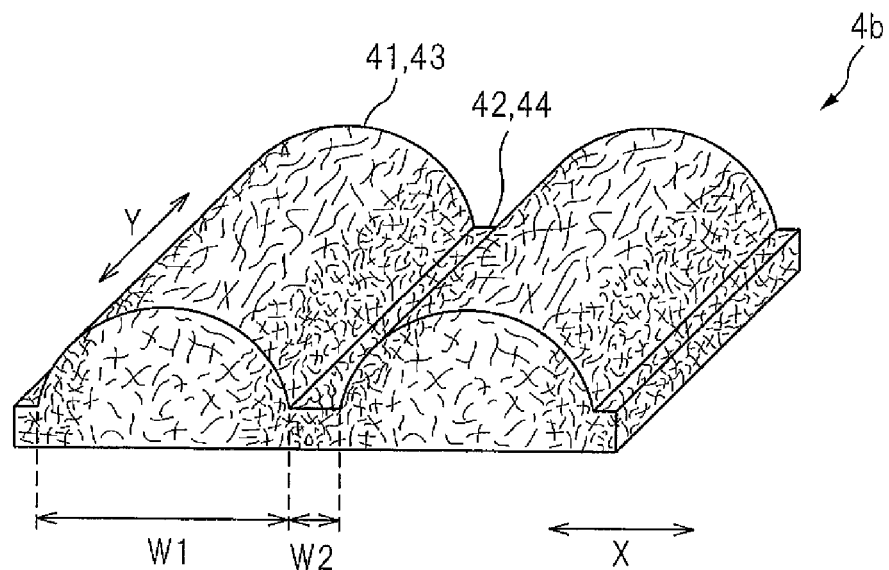
FIG. 5 is a perspective view showing a ridge-furrow structure of an absorbent body to be used in a sanitary napkin according to a second embodiment of the invention.

The widths of the ridges 41,43 (W1 in FIG. 5) are preferably 0.5 to 10 mm and more preferably 2 to 5 mm, from the viewpoint of liquid migration from the top sheet 2. From the same viewpoint, the widths of the furrows 42,44 (W2 in FIG. 5) are preferably 0.1 to 10 mm and more preferably 1 to 5 mm.

Figure 6:
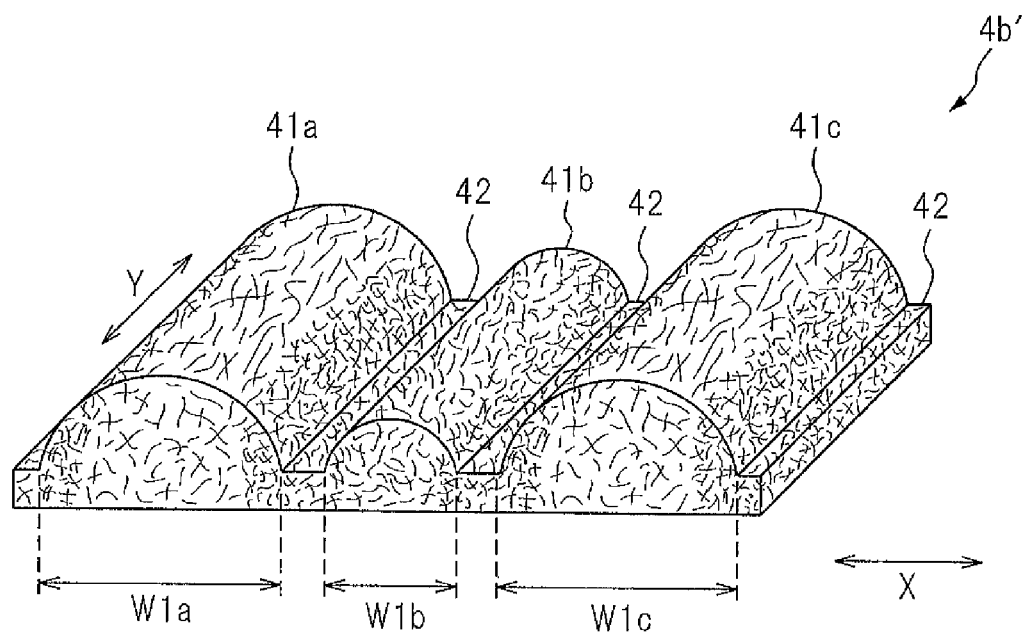
FIG. 6 is a perspective view showing a modified example of a ridge-furrow structure of an absorbent body.

In the absorbent body $4b$, the width of each ridge 41, the width of each ridge 43, the width of each furrow 42 and the width of each furrow 44 are approximately equal, but they may be different. For example, in the absorbent body $4b'$ as a modified example of the absorbent body $4b$, shown in FIG. 6, the width W1$a$ of the ridge 41$a$ differs from the width W1$b$ of another ridge 41$b$, but it may be approximately the same as the width W1$c$ of yet another ridge 41$c$. The same modification is possible for the ridge 43 and the furrows 42,44.

Figure 7:
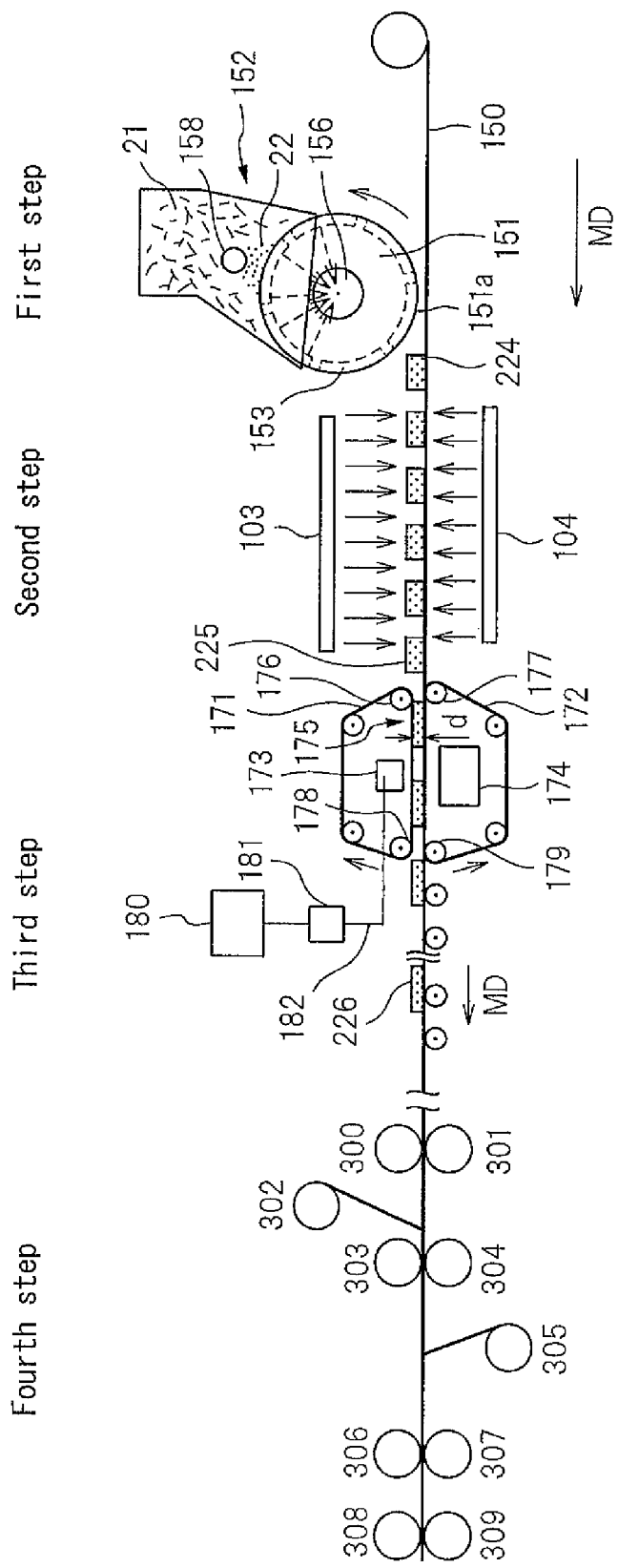
FIG. 7 is a diagram showing production steps for an absorbent body and an absorbent article.

A concrete example of production steps for sanitary napkins according to the first embodiment to third embodiment will now be described based on FIG. 7.

[First Step]

Recesses 153 are formed at a prescribed pitch in the circumferential direction on the peripheral surface 151$a$ of a suction drum 151 rotating in the machine direction MD, as a mold in which the absorbent body material is to be packed. When the suction drum 151 is rotated and the recesses 153 approach the material feeder 152, the suction section 156 acts on the recesses and the absorbent body material supplied from the material feeder 152 is vacuum suctioned into the recesses 153.

The hooded material feeder 152 is formed so as to cover the suction drum 151, and the material feeder 152 supplied a mixed material 21 comprising cellulose-based water-absorbent fibers and thermoplastic resin fibers into the recesses 153 by air transport. The material feeder 152 is also provided with a particle feeder 158 that supplies superabsorbent polymer particles 22, so that superabsorbent polymer particles 22 are supplied to the recesses 153. The cellulose-based water-absorbent fibers, thermoplastic resin fibers and superabsorbent polymer particles are supplied in a mixed state to the recesses 153, and a layered material 224 is formed in the recesses 153. The layered material 224 formed in the recesses 153 is transferred onto a carrier sheet 150 advancing in the machine direction MD.

[Second Step]

The layered material 224 that has been transferred onto the carrier sheet 150 separates from the peripheral surface 151$a$ of the suction drum 151 and is transported in the machine direction MD. The uncompressed layered material 224 is arranged intermittently in the machine direction MD in the carrier sheet 150. A heating section 103 injects air heated to 135° C. at a wind speed of 5 m/sec onto the top side of the layered material 224 while a heating section 104 injects it onto the bottom side of the layered material 224. This melts the thermoplastic resin fibers in the layered material 224, forming a layered material 225 in which the thermoplastic resin fibers, the thermoplastic resin fibers/pulp and the thermoplastic resin fibers/superabsorbent polymer particles are bonded (heat fused). The conditions for the heated air injected onto the layered material 224 (the temperature, wind speed and heating time) are appropriately controlled depending on the production rate.

[Third Step]

The air-permeable mesh conveyor belts 171,172 disposed above and below, forming a pair, transport the layered material 225 on the carrier sheet 150 in the machine direction MD, while compacting it. The dimensions in the vertical direction d for the parallel traveling section 175 (the distance between the mesh conveyor belts 171,172) are set to prescribed values by adjusting the gap between the upstream end upper roll 176 and the upstream end lower roll 177, and the gap between the downstream end upper roll 178 and the downstream end lower roll 179, which rotate in the machine direction MD, and the layered material 225 is compacted to a prescribed thickness by the mesh conveyor belts 171,172. At the parallel traveling section 175 that extends horizontally, as shown in FIG. 7, a steam injecting section 173 and a steam suction section 174 are disposed facing and sandwiching the mesh conveyor belts 171,172. At the steam injecting section 173, nozzles of 0.1 to 2 mm caliber (not shown) are disposed in the crossing direction CD (not shown) which runs perpendicular to the machine direction MD and the vertical direction TD, transversing the layered material 225 at a pitch of 0.5 to 10 mm, preferably 0.5 to 5 mm and more preferably 0.5 to 3 mm, and each nozzle has water vapor at a temperature above the boiling point of the water, generated at a steam boiler 180, which is converted to high-pressure steam adjusted to a vapor pressure of 0.1 to 2.0 MPa, for example, by a pressure control valve 181, and supplied through tubing 182. From each nozzle there is injected high-pressure steam through the mesh conveyor belt 171, onto the layered material 225 which is in a compacted state by the mesh conveyor belts 171,172. The amount of high-pressure steam injected onto the layered material 225 is adjusted according to the running speed of the mesh conveyor belts 171,172, and preferably when the mesh conveyor belts 171,172 are traveling at 5 to 500 m/min, injecting is in a range of 1.23 kg/m$^2$ to 0.03 kg/m$^2$ on the surface area of the layered material 225 facing the mesh conveyor belt 171. The water vapor passes through the mesh conveyor belt 171, the layered material 225 and the mesh conveyor belt 172 in that order in the thickness direction of the layered material 225, and is collected by vacuum pressure suction action at the steam suction section 174. The layered material 225 on which the high-pressure steam has been injected advances in the machine direction MD and separates from the mesh conveyor belts 171,172, proceeding to the fourth step. Ridges and furrows are formed on the surface of the layered material 225 on which the high-pressure steam has been injected. By adjusting the number of nozzles and their pitch in the steam injecting section 173, it is possible to adjust the number of ridges and furrows and their spacings. The sections where the high-pressure steam has been injected become the furrows.

Either or both of the mesh conveyor belts 171,172 has a flexible property so as to easily deform in the vertical direction TD, so that the layered material 225 is not locally compacted by the mesh conveyor belts 171,172 in the third step. The mesh conveyor belts 171,172 used may be metal wire mesh belts formed of stainless steel alloy or bronze, or plastic mesh belts formed of polyester fiber or aramid fiber, or alternatively metal belts formed of perforated metal plates may be used instead of mesh belts. If inclusion of metal powder in the layered material 225 is to be maximally avoided, it is preferred to use a plastic mesh belt. Also, when high heat resistance is desired for a plastic mesh belt, it is preferred to use a mesh belt made of a polyphenylene sulfide resin. A 10 to 75 mesh plain weave mesh belt using a polyphenylene sulfide resin is a particularly preferred example of a mesh belt which has flexibility and can be used for both the mesh conveyor belt 171 and the mesh conveyor belt 172. The steam injecting section 173 and the tubing 182 are preferably heat-insulated as appropriate, and are preferably also provided with a draining mechanism. This can prevent drain from the steam injecting section 173 from being injected from the nozzle and causing excessive moisture to be incorporated into the layered material 225. The water vapor injected toward the layered material 225 will be sometimes dry vapor containing no liquid moisture, sometimes saturated vapor, and sometimes wet vapor containing moisture. When the water vapor is wet vapor or saturated vapor it is easier to wet the pulp to allow shaping. Dry vapor can gasify the moisture in the pulp, and allows shaping of the pulp to be easily accomplished with the gasified moisture. If the pulp is thermoplastic synthetic fiber, the heat of the dry vapor can facilitate shaping of the thermoplastic synthetic fibers. The steam injecting section 173 has a heating mechanism provided in it, and it can convert the water vapor to superheated steam and inject it. The steam suction section 174 preferably has tubing that directs toward an exhaust blower (not shown) after the aspirated high-pressure steam has passed through a steam separator. Incidentally, the positioning of the steam injecting section 173 and the steam suction section 174 may be switched, i.e. the steam injecting section 173 may be below and the steam suction section 174 above. When the high-pressure steam does not need to be recovered, the process may be carried out without provision of the steam suction 174 section.

[Fourth Step]

The fourth step is an example of a common step for producing a sanitary napkin. A pair of rolls 300,301 punch out the absorbent body 226 obtained in the third step, into a prescribed shape. A top sheet is supplied from a roll 302 and sealed with hot embossers 303,304 having high compression section and a low compression section, and the top sheet and absorbent body 226 are integrated. Next, a back sheet 305 is supplied, and with the absorbent body 226 sandwiched between a top sheet and a back sheet, the product perimeter is subjected to hot embossing for sealing and passed to steps 306 and 307, and finally cut into the product shape by steps 308 and 309.

<Fourth Embodiment>

According to the fourth embodiment, a blood modifying agent is coated onto the surface of the top sheet 2.

The viscosity and surface tension of menstrual blood are lowered by the blood modifying agent, and menstrual blood that has been excreted into the top sheet 2 rapidly migrates from the top sheet 2 to the absorbent body and is absorbed into the absorbent body. The increased absorption rate of menstrual blood into the absorbent body minimizes residue of highly viscous menstrual blood into the top sheet, reduces stickiness of the top sheet 2 and improves the surface drying property of the top sheet 2. In addition, highly viscous menstrual blood lumps do not easily remain on the top sheet 2, and the wearer is not easily left with a visually unpleasant image. Furthermore, it is possible to inhibit leakage of menstrual blood excreted into the top sheet 2, from the widthwise direction side of the sanitary napkin 1.

The region coated with the blood modifying agent may be the entirety of the surface of the top sheet 2 or only a portion thereof, but preferably it includes at least the region contacting the excretory opening (vaginal opening) of the user.

The coated basis weight of the blood modifying agent on the top sheet 2 is preferably 1 to 30 g/m² and more preferably 3 to 10 g/m². If the coating basis weight of the blood modifying agent is smaller than 1 g/m², it may be difficult to coat the blood modifying agent on the top sheet 2 in a stable manner, and if the coating basis weight of the blood modifying agent is greater than 30 g/m², the top sheet 2 may become greasy.

The method of coating the blood modifying agent may be, for example, a method of heating the blood modifying agent to a prescribed temperature, and then coating it using a contact coater such as a slot coater, or a non-contact coater such as a spray coater, curtain coater or spiral coater. A method of coating using a non-contact coater is preferred from the viewpoint of allowing the blood modifying agent to be evenly dispersed as droplets in the top sheet 2, and not incurring damage to the top sheet 2.

There are no particular restrictions on the time point at which the blood modifying agent is coated onto the top sheet 2, but from the viewpoint of limiting equipment investment, the blood modifying agent is preferably coated onto the top sheet 2 in the step of producing the sanitary napkin 1. When the blood modifying agent is to be coated onto the top sheet 2 in the step of producing the sanitary napkin 1, the blood modifying agent is preferably coated onto the top sheet 2 in a step near the final step, from the viewpoint of avoiding reduction in the blood modifying agent. For example, the top sheet 2 may be coated with the blood modifying agent just before the step of wrapping the sanitary napkin 1.

When hydrophobic synthetic fibers are used in the top sheet 2, in consideration of permeability of liquid excreta and rewet-back, a hydrophilic agent or water-repellent agent may be kneaded with the hydrophobic synthetic fibers, or the hydrophobic synthetic fibers may be coated with a hydrophilic agent, water-repellent agent or the like. The hydrophobic synthetic fibers may also be rendered hydrophilic by corona treatment or plasma treatment. This will allow the hydrophilic areas and lipophilic areas to be mutually isolated in the blood modifying agent-coated region when the blood modifying agent is lipophilic, and both the hydrophilic components (mainly plasma) and lipophilic components (mainly blood cells) in menstrual blood will rapidly migrate from the top sheet 2 into the absorbent body.

The blood modifying agent will now be explained in detail.
<Blood Modifying Agent>

The blood modifying agent of the present invention has an IOB of about 0.00-0.60, a melting point of about 45° C. or less, and a water solubility of about 0.00-0.05 g in 100 g of water at 25° C.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| CH₂ | 0 | 20 |
| iso-branch | 0 | −10 |
| tert-branch | 0 | −20 |
| Light metal (salt) | ≥500 | 0 |
| Heavy metal (salt), amine, NH₃ salt | ≥400 | 0 |

For example, in the case of an ester of tetradecanoic acid which has 14 carbon atoms and dodecyl alcohol which has 12 carbon atoms, the organic value is 520 (CH₂, 20×26) and the inorganic value is 60 (—COOR, 60×1), and therefore IOB=0.12.

In the blood modifying agent, the IOB is about 0.00-0.60, preferably about 0.00-0.50, more preferably about 0.00-0.40 and even more preferably about 0.00-0.30. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood modifying agent has a melting point of about 45° C. or less, it may be either liquid or solid at room temperature, or in other words, the melting point may be either about 25° C. or higher or below about 25° C., and for example, it may have a melting point of about −5° C. or about −20° C. The reason why the blood modifying agent should have a melting point of about 45° C. or less will be explained below.

The blood modifying agent does not have a lower limit for the melting point, but the vapor pressure is preferably low. The vapor pressure of the blood modifying agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere). Considering that the absorbent article is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure is high, gasification may occur during storage and the amount of blood modifying agent may be reduced, and as a consequence problems, such as odor during wear, may be created.

The melting point of the blood modifying agent may also differ depending on the weather or duration of wear. For example, in regions with a mean atmospheric temperature of about 10° C. or less, using a blood modifying agent with a melting point of about 10° C. or less may allow the blood modifying agent to stably modify blood after excretion of menstrual blood, even if it has been cooled by the ambient temperature.

Also, when the absorbent article is used for a prolonged period of time, the melting point of the blood modifying agent is preferably at the high end of the range of about 45° C. or less. This is because the blood modifying agent is not easily affected by sweat or friction during wearing, and will not easily migrate even during prolonged wearing.

A water solubility of 0.00-0.05 g can be confirmed by adding 0.05 g of sample to 100 g of deionized water at 25° C., allowing the mixture to stand for 24 hours, and gently stirring after 24 hours if necessary and then visually evaluating whether or not the sample has dissolved.

The term "solubility" used herein in regard to water solubility includes cases where the sample completely dissolves in deionized water to form a homogeneous mixture, and cases where the sample is completely emulsified. Here, "completely" means that no mass of the sample remains in the deionized water.

In the art, top sheet surfaces are coated with surfactants in order to alter the surface tension of blood and promote rapid absorption of blood. However, because surfactants generally have high water solubility, the surfactant-coated top sheet is highly miscible with hydrophilic components (such as, blood plasma) in the blood and therefore, instead, they tend to cause residue of blood on the top sheet. The aforementioned blood modifying agent has low water solubility and therefore, unlike conventionally known surfactants, it does not cause residue of blood on the top sheet and allows rapid migration into the absorbent body.

As used herein, a water solubility in 100 g of water at 25° C. may be simply referred to as "water solubility".

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.

Columns: SHODEX KF-801, KF-803 and KF-804, by Showa

Denko K.K.

Eluent: THF

Flow rate: 1.0 mL/min

Driving volume: 100 μL

Detection: RI (differential refractometer)

The weight-average molecular weights listed in the examples of the present specification were measured under the conditions described below.

Preferably, the blood modifying agent is selected from the group consisting of following items (i)-(iii), and combinations thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituted for a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). As shown in Table 1, the carboxyl groups bond with metals and the like in menstrual blood, drastically increasing the inorganic value from 150 to 400 or greater, and therefore a blood modifying agent with carboxyl groups can increase the IOB value to more than about 0.60 during use, potentially lowering the affinity with blood cells.

More preferably, the blood modifying agent is selected from the group consisting of following items (i')-(iii'), and combinations thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituted for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood modifying agent is more preferably a compound with not more than about 1.8 carbonyl bonds (—CO—), not more than 2 ester bonds (—COO—), not more than about 1.5 carbonate bonds (—OCOO—), not more than about 6 ether bonds (—O—), not more than about 0.8 carboxyl groups (—COOH) and/or not more than about 1.2 hydroxyl groups (—OH), per 10 carbon atoms in the hydrocarbon moiety.

Even more preferably, the blood modifying agent is selected from the group consisting of following items (A)-(F), and combinations thereof:

(A) an ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety;

(B) an ether of (B1) a compound having a chain hydrocarbon moiety and 2-4 hydroxyl groups substituted for hydrogens on the chain hydrocarbon moiety, and (B2) a compound having a chain hydrocarbon moiety and 1 hydroxyl group substituted for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituted for hydrogens on the chain hydrocarbon moiety, and (C2) a compound having a chain hydrocarbon moiety and 1 hydroxyl group substituted for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_2$-$C_6C_{2-6}$ alkylene glycol, or its ester or ether; and (F) a chain hydrocarbon.

The blood modifying agent in accordance with (A) to (F) will now be described in detail.

[(A) Ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety]

In the (A) ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety (hereunder also referred to as "compound (A)"), it is not necessary for all of the hydroxyl groups to be esterified so long as the IOB, melting point and water solubility are within the aforementioned ranges.

Examples of (A1) a compound having a chain hydrocarbon moiety and 2-4 hydroxyl groups substituted for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituted for a hydrogen on the chain hydrocarbon moiety (hereunder also referred to as "compound (A2)") include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

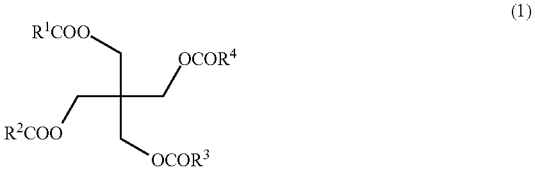

(1)

triesters of pentaerythritol and fatty acids, represented by the following formula (2):

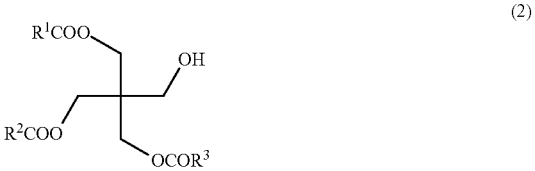

(2)

diesters of pentaerythritol and fatty acids, represented by the following formula (3):

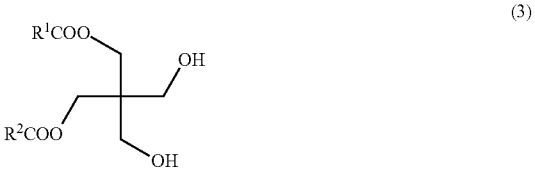

(3)

and monoesters of pentaerythritol and fatty acids, represented by the following formula (4).

(4)

In the formulas, $R^1$-$R^4$ each represent a chain hydrocarbon.

The fatty acids consisting of the esters of pentaerythritol and fatty acids ($R^1$COOH, $R^2$COOH, $R^3$COOH, and $R^4$COOH) are not particularly restricted so long as the pentaerythritol and fatty acid esters satisfy the conditions for the IOB, melting point and water solubility, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1$C, $R^2$C, $R^3$C or $R^4$C, same hereunder), propanoic acid ($C_3$), butanoic acid ($C_4$) and its isomers, such as 2-methylpropanoic acid ($C_4$), pentanoic acid ($C_5$) and its isomers, such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers of the foregoing (excluding those mentioned above).

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, in order to lower the IOB and result in greater hydrophobicity, the ester of pentaerythritol and a fatty acid is preferably a diester, triester or tetraester, more preferably a triester or tetraester, and even more preferably a tetraester.

In a tetraester of pentaerythritol and a fatty acid, the IOB is 0.60 if the total number of carbons of the fatty acid consisting of the tetraester of the pentaerythritol and fatty acid, i.e., the total number of carbons of the $R^1C$, $R^2C$, $R^3C$ and $R^4C$ portions in formula (1), is 15. Thus, when the total number of carbons of the fatty acid consisting of the tetraester of the pentaerythritol and fatty acid is approximately 15 or greater, the IOB satisfies the condition of being within about 0.00 to 0.60.

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

In a triester of pentaerythritol and a fatty acid, the IOB is 0.58 if the total number of carbons of the fatty acid consisting of the triester of the pentaerythritol and fatty acid, i.e., the total number of carbons of the $R^1C$, $R^2C$ and $R^3C$ portions in formula (2), is 19. Thus, when the total number of carbons of the fatty acid consisting of the triester of the pentaerythritol and fatty acid is approximately 19 or greater, the IOB satisfies the condition of being within about 0.00 to 0.60.

In a diester of pentaerythritol and a fatty acid, the IOB is 0.59 if the total number of carbons of the fatty acid consisting of the diester of the pentaerythritol and fatty acid, i.e., the total number of carbons of the $R^1C$ and $R^2C$ portion in formula (3), is 22. Thus, when the total number of carbons of the fatty acid consisting of the diester of the pentaerythritol and fatty acid is approximately 22 or greater, the IOB satisfies the condition of being within about 0.00 to 0.60.

In a monoester of pentaerythritol and a fatty acid, the IOB is 0.60 if the total number of carbons of the fatty acid consisting of the monoester of the pentaerythritol and fatty acid, i.e. the total number of carbons of the $R^1C$ portion in formula (4), is 25. Thus, when the number of carbons of the fatty acid consisting of the monoester of the pentaerythritol and fatty acid is approximately 25 or greater, the IOB satisfies the condition of being within about 0.00 to 0.60.

The effects of double bonds, triple bonds, iso-branches and tert-branches are not considered in this calculation.

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

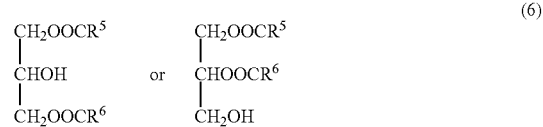

and monoesters of glycerin and fatty acids, represented by the following formula (7):

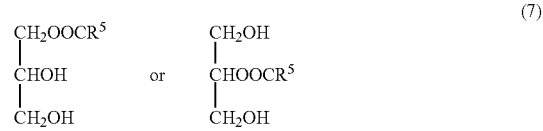

wherein $R^5$-$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the IOB, melting point and water solubility, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, in order to lower the IOB and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of about 45° C. or less, preferred triesters of glycerin and fatty acids are those with not more than about 40 as the total number of carbons of the fatty acid consisting of the triester of glycerin and the fatty acid, i.e., the total number of carbons of the $R^5C$, $R^6C$ and $R^7C$ sections in formula (5).

In a triester of glycerin and a fatty acid, the IOB value is 0.60 when the total number of carbons of the fatty acid consisting of the triester of glycerin and the fatty acid, i.e., the total number of carbons of the $R^5C$, $R^6C$ and $R^7C$ portions in formula (5), is 12. Thus, when the total number of carbons of the fatty acid consisting of the triester of the glycerin and fatty acid is approximately 12 or greater, the IOB satisfies the condition of being within about 0.00 to 0.60.

Triesters of glycerin and fatty acids, being aliphatic and therefore potential constituent components of the human body are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

In a diester of glycerin and a fatty acid, the IOB is 0.58 if the total number of carbons of the fatty acid consisting of the diester of the glycerin and fatty acid, i.e., the total number of carbons of the $R^5C$ and $R^6C$ portions in formula (6), is 16. Thus, when the total number of carbons of the fatty acid consisting of the diester of the glycerin and fatty acid is approximately 16 or greater, the IOB satisfies the condition of being about 0.00 to 0.60.

Monoesters of glycerin and fatty acids are also known as monoglycerides, and examples include glycerin and eicosanoic acid ($C_{20}$) monoester, and glycerin and docosanoic acid ($C_{22}$) monoester.

In a monoester of glycerin and a fatty acid, the IOB is 0.59 if the total number of carbons of the fatty acid consisting of the monoester of the glycerin and fatty acid, i.e. the number of carbons of the $R^5C$ portion in formula (7), is 19. Thus, when the number of carbons of the fatty acid consisting of the monoester of the glycerin and fatty acid is approximately 19 or greater, the IOB satisfies the condition of being about 0.00 to 0.60.

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

$$R^8COOC_kH_{2k}OCOR^9 \qquad (8)$$

wherein k represents an integer of 2-6, and $R^8$ and $R^9$ each represent a chain hydrocarbon,
and monoesters of $C_2$-$C_6$ glycols and fatty acids, represented by the following formula (9):

$$R^8COOC_kH_{2k}OH \qquad (9)$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the IOB, melting point and water solubility, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

In a diester of butylene glycol (k=4) and a fatty acid represented by formula (8), IOB is 0.60 when the total number of carbons of the $R^8C$ and $R^9C$ portions is 6. Thus, when the total number of carbon atoms in a diester of butylene glycol (k=4) and a fatty acid represented by formula (8) is approximately 6 or greater, the IOB satisfies the condition of being about 0.00-0.60. In a monoester of ethylene glycol (k=2) and a fatty acid represented by formula (9), IOB is 0.57 when the total number of carbons of the $R^8C$ portion is 12. Thus, when the total number of carbon atoms in the fatty acid consisting of a monoester of ethylene glycol (k=2) and a fatty acid represented by formula (9) is approximately 12 or greater, the IOB satisfies the condition of being about 0.00-0.60.

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, in order to lower the IOB and result in greater hydrophobicity, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, in order to lower the IOB and result in greater hydrophobicity, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a compound having a chain hydrocarbon moiety and 2-4 hydroxyl groups substituted for hydrogens on the chain hydrocarbon moiety and (B2) a compound having a chain hydrocarbon moiety and 1 hydroxyl group substituted for a hydrogen on the chain hydrocarbon moiety]

In the (B) ether of (B1) a compound having a chain hydrocarbon moiety and 2-4 hydroxyl groups substituted for hydrogens on the chain hydrocarbon moiety and (B2) a compound having a chain hydrocarbon moiety and 1 hydroxyl group substituted for a hydrogen on the chain hydrocarbon moiety (hereunder also referred to as "compound (B)"), it is not necessary for all of the hydroxyl groups to be etherified so long as the IOB, melting point and water solubility are within the aforementioned ranges.

Examples of (B1) a compound having a chain hydrocarbon moiety and 2-4 hydroxyl groups substituted for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituted for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and its isomers, including isopropyl alcohol ($C_3$), butyl alcohol ($C_4$) and its isomers, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and its isomers, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C=C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

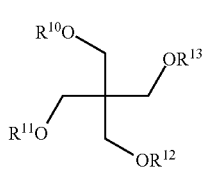

(10)

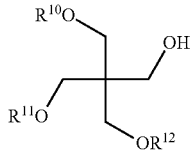

(11)

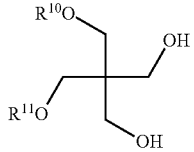

(12)

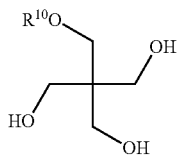

(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

$$\begin{array}{l} CH_2OR^{14} \\ | \\ CHOR^{15} \\ | \\ CH_2OR^{16} \end{array} \quad (14)$$

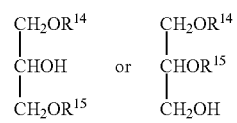

(15)

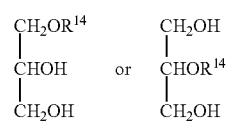

(16)

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

In the tetraether of pentaerythritol and an aliphatic monohydric alcohol, the IOB is 0.44 when the total number of carbon atoms of the aliphatic monohydric alcohol consisting of the tetraether of pentaerythritol and the aliphatic monohydric alcohol, i.e., the total number of carbon atoms of the $R^{10}$, $R^{11}$, $R^{12}$ and $R^{13}$ portions in formula (10), is 4. Thus, when the total number of carbon atoms of the aliphatic monohydric alcohol consisting of a tetraether of pentaerythritol and an aliphatic monohydric alcohol is approximately 4 or greater, the IOB value satisfies the condition of being within about 0.00 to 0.60.

In the triether of pentaerythritol and an aliphatic monohydric alcohol, the IOB is 0.57 when the total number of carbon atoms of the aliphatic monohydric alcohol consisting of the triether of pentaerythritol and the aliphatic monohydric alcohol, i.e., the total number of carbon atoms of the $R^{10}$, $R^{11}$ and $R^{12}$ portions in formula (11), is 9. Thus, when the total number of carbon atoms of the aliphatic monohydric alcohol consisting of a triether of pentaerythritol and an aliphatic monohydric alcohol is approximately 9 or greater, the IOB value satisfies the condition of being within about 0.00 to 0.60.

In the diether of pentaerythritol and an aliphatic monohydric alcohol, the IOB is 0.60 when the total number of carbon atoms of the aliphatic monohydric alcohol consisting of the diether of pentaerythritol and the aliphatic monohydric alcohol, i.e., the total number of carbon atoms of the $R^{10}$ and $R^{11}$ portions in formula (12), is 15. Thus, when the total number of carbon atoms of the aliphatic monohydric alcohol consisting of a diether of pentaerythritol and an aliphatic monohydric alcohol is approximately 15 or greater, the IOB value satisfies the condition of being within about 0.00 to 0.60.

In the monoether of pentaerythritol and an aliphatic monohydric alcohol, the IOB is 0.59 when the number of carbon atoms of the aliphatic monohydric alcohol consisting of the monoether of pentaerythritol and the aliphatic monohydric alcohol, i.e. the number of carbon atoms of the $R^{10}$ portion in formula (13), is 22. Thus, when the total number of carbon atoms of the aliphatic monohydric alcohol consisting of a monoether of pentaerythritol and an aliphatic monohydric alcohol is approximately 22 or greater, the IOB value satisfies the condition of being within about 0.00 to 0.60.

In the triether of glycerin and an aliphatic monohydric alcohol, the IOB is 0.50 when the total number of carbon atoms of the aliphatic monohydric alcohol consisting of the triether of glycerin and the aliphatic monohydric alcohol, i.e., the total number of carbon atoms of the $R^{14}$, $R^{15}$ and $R^{16}$ portions in formula (14), is 3. Thus, when the total number of carbon atoms of the aliphatic monohydric alcohol consisting of a triether of glycerin and an aliphatic monohydric alcohol is approximately 3 or greater, the IOB value satisfies the condition of being within about 0.00 to 0.60.

In the diether of glycerin and an aliphatic monohydric alcohol, the IOB is 0.58 when the total number of carbon atoms of the aliphatic monohydric alcohol consisting of the diether of glycerin and the aliphatic monohydric alcohol, i.e., the total number of carbon atoms of the $R^{14}$ and $R^{15}$ portions in formula (15), is 9. Thus, when the total number of carbon atoms of the aliphatic monohydric alcohol consisting of a diether of glycerin and an aliphatic monohydric alcohol is approximately 9 or greater, the IOB value satisfies the condition of being within about 0.00 to 0.60.

In the monoether of glycerin and an aliphatic monohydric alcohol, the IOB is 0.58 when the number of carbon atoms of the aliphatic monohydric alcohol consisting of the monoether of glycerin and the aliphatic monohydric alcohol, i.e., the number of carbon atoms of the $R^{14}$ portion in formula (16), is 16. Thus, when the total number of carbon atoms of the aliphatic monohydric alcohol consisting of a monoether of glycerin and an aliphatic monohydric alcohol is approximately 16 or greater, the IOB value satisfies the condition of being within about 0.00 to 0.60.

In a diether of butylene glycol (n=4) and aliphatic monohydric alcohol represented by formula (17), the IOB is 0.33 when the total number of carbon atoms of the $R^{17}$ and $R^{18}$ portions is 2. Thus, when the number of carbon atoms of the aliphatic monohydric alcohol in a diether of butylene glycol (n=4) and an aliphatic monohydric alcohol represented by formula (17) is approximately 2 or greater, the IOB value satisfies the condition of being within about 0.00-0.60. Also, in a monoether of ethylene glycol (n=2) and aliphatic monohydric alcohol represented by formula (18), the IOB is 0.60 when the number of carbon atoms of the $R^{17}$ portion is 8. Thus, when the number of carbon atoms of the aliphatic monohydric alcohol consisting of a monoether of ethylene glycol (n=2) and an aliphatic monohydric alcohol represented by formula (18) is approximately 8 or greater, the IOB value satisfies the condition of being within about 0.00 to 0.60.

Compound (B) may be produced by dehydrating condensation of compound (B1) and compound (B2) in the presence of an acid catalyst.

[(C) Ester of (C1) a carboxylic acid, hydroxy acid, alkoxy acid or oxoacid comprising a chain hydrocarbon moiety and 2-4 carboxyl groups substituted for hydrogens on the chain hydrocarbon moiety and (C2) a compound having a chain hydrocarbon moiety and 1 hydroxyl group substituted for a hydrogen on the chain hydrocarbon moiety]

In the (C) ester of (C1) a carboxylic acid, hydroxy acid, alkoxy acid or oxoacid comprising a chain hydrocarbon moiety and 2-4 carboxyl groups substituted for hydrogens on the chain hydrocarbon moiety and (C2) a compound having a chain hydrocarbon moiety and 1 hydroxyl group substituted for a hydrogen on the chain hydrocarbon moiety (hereunder also referred to as "compound (C)"), it is not necessary for all of the carboxyl groups to be esterified so long as the IOB, melting point and water solubility are within the aforementioned ranges.

Examples of (C1) a carboxylic acid, hydroxy acid, alkoxy acid or oxoacid comprising a chain hydrocarbon moiety and 2-4 carboxyl groups substituted for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituted for a hydrogen on the chain hydrocarbon moiety includes those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, (c₂) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or (c₃) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, diisostearyl malate, tributyl citrate and tributyl O-acetylcitrate, of which commercially available products exist.

[(D) Compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be (d₁) an ether of an aliphatic monohydric alcohol and an aliphatic monohydric alcohol, (d₂) a dialkyl ketone, (d₃) an ester of a fatty acid and an aliphatic monohydric alcohol, or (d₄) a dialkyl carbonate.

[(d₁) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \qquad (19)$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the IOB, melting point and water solubility, and for example, it may be one of the aliphatic monohydric alcohols mentioned for "compound (B)".

In an ether of an aliphatic monohydric alcohol and an aliphatic monohydric alcohol, the IOB is 0.50 when the total number of carbon atoms of the aliphatic monohydric alcohols consisting of the ether, i.e., the total number of carbons of the $R^{19}$ and $R^{20}$ portions in formula (19), is 2, and therefore when the total number of carbons of the aliphatic monohydric alcohols consisting of the ether is about 2 or greater, this condition for the IOB is satisfied. However, when the total number of carbons of the aliphatic monohydric alcohols consisting of the ether is about 6, the water solubility is as high as about 2 g, which is problematic from the viewpoint of vapor pressure as well. In order to satisfy the condition of a water solubility of about 0.00-0.05 g, the total number of carbons of the aliphatic monohydric alcohols consisting of the ether is preferably about 8 or greater.

[(d₂) Dialkyl Ketone]

The dialkyl ketone may be a compound of the following formula (20):

$$R^{21}COR^{22} \qquad (20)$$

wherein $R^{21}$ and $R^{22}$ are each an alkyl group.

In a dialkyl ketone, the IOB is 0.54 when the total number of carbon atoms of $R^{21}$ and $R^{22}$ is 5, and therefore this condition for the IOB is satisfied if the total number of carbons is about 5 or greater. However, when the total number of carbons of dialkyl ketone is about 5, the water solubility is as high as about 2 g. Therefore, in order to satisfy the condition of a water solubility of about 0.00-0.05 g, the total number of carbons of dialkyl ketone is preferably about 8 or greater. In consideration of vapor pressure, the number of carbon atoms of dialkyl ketone is preferably about 10 or greater and more preferably about 12 or greater.

If the total number of carbon atoms of dialkyl ketone is about 8, such as in 5-nonanone, for example, the melting point is approximately −50° C. and the vapor pressure is about 230 Pa at 20° C.

The dialkyl ketone may be a commercially available product, or it may be obtained by a known method, such as by oxidation of a secondary alcohol with chromic acid or the like.

[(d₃) Ester of a Fatty Acid and an Aliphatic Monohydric Alcohol]

Examples of esters of a fatty acid and an aliphatic monohydric alcohol include compounds having the following formula (21):

$$R^{23}COOR^{24} \qquad (21)$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "(a₁) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

In an ester of such a fatty acid and aliphatic monohydric alcohol, the IOB is 0.60 when the total number of carbon atoms of the fatty acid and aliphatic monohydric alcohol, i.e. the total number of carbon atoms of the $R^{23}C$ and $R^{24}$ portions in formula (21), is 5, and therefore this condition for the IOB is satisfied when the total number of carbon atoms of the $R^{23}C$ and $R^{24}$ portions is about 5 or greater. However, with butyl acetate in which the total number of carbon atoms is 6, the vapor pressure is high at greater than 2,000 Pa. In consideration of vapor pressure, therefore, the total number of carbon atoms is preferably about 12 or greater. If the total number of carbon atoms is about 11 or greater, it will be possible to satisfy the condition of a water solubility of about 0.00-0.05 g.

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[(d₄) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

In a dialkyl carbonate, the IOB is 0.57 when the total number of carbon atoms of $R^{25}$ and $R^{26}$ is 6, and therefore this condition for the IOB is satisfied if the total number of carbons of $R^{25}$ and $R^{26}$ is about 6 or greater.

In consideration of water solubility, the total number of carbon atoms of $R^{25}$ and $R^{26}$ is preferably about 7 or greater and more preferably about 9 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Polyoxy $C_2$-$C_6$ alkylene glycol, or alkyl ester or alkyl ether thereof]

The (E) polyoxy $C_2$-$C_6$ alkylene glycol, or alkyl ester or alkyl ether thereof (hereunder also referred to as "compound (E)") may be ($e_1$) a polyoxy $C_2$-$C_6$ alkylene glycol, ($e_2$) an ester of a polyoxy $C_2$-$C_6$ alkylene glycol and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycol and a chain hydrocarbon tetracarboxylic acid, chain hydrocarbon tricarboxylic acid or chain hydrocarbon dicarboxylic acid, or ($e_5$) an ether of a polyoxy $C_2$-$C_6$ alkylene glycol and a chain hydrocarbon tetraol, chain hydrocarbon triol or chain hydrocarbon diol. These will now be explained.

[($e_1$) Polyoxy $C_2$-$C_6$ Alkylene Glycol]

Polyoxy $C_2$-$C_6$ alkylene glycols refer to i) one or more homopolymers having a unit selected from the group consisting of oxy $C_2$-$C_6$ alkylene units, such as oxyethylene unit, oxypropylene unit, oxybutylene unit, oxypentylene unit and oxyhexylene unit and having hydroxyl groups at both ends, ii) one or more block copolymers having 2 or more units selected from oxy $C_2$-$C_6$ alkylene units described above and oxyhexylene unit and having hydroxyl groups at both ends, or iii) random copolymers having 2 or more units selected from oxy $C_2$-$C_6$ alkylene units described above and having hydroxyl groups at both ends.

The oxy $C_2$-$C_6$ alkylene units are preferably oxypropylene unit, oxybutylene unit, oxypentylene unit or oxyhexylene unit, and more preferably oxybutylene unit, oxypentylene unit and oxyhexylene unit, from the viewpoint of reducing the value of IOB.

The polyoxy $C_2$-$C_6$ alkylene glycol can be represented by the following formula (23):

$$HO\text{---}(C_mH_{2m}O)_n\text{---}H \qquad (23)$$

wherein m represents an integer of 2-6.

The present inventors have confirmed that in polyethylene glycol (corresponding to the homopolymer of formula (23) where m=2), when n≥45 (the weight-average molecular weight exceeds about 2,000), the condition for IOB of about 0.00 to about 0.60 is satisfied, but the condition for the water solubility is not satisfied even when the weight-average molecular weight exceeds about 4,000. Therefore, ethylene glycol homopolymer is not included in the ($e_1$) polyoxy $C_2$-$C_6$ alkylene glycol, and ethylene glycol should be included in the ($e_1$) polyoxy $C_2$-$C_6$ alkylene glycol only as a copolymer or random polymer with another glycol.

Thus, homopolymers of formula (23) may include propylene glycol, butylene glycol, pentylene glycol or hexylene glycol homopolymer.

For this reason, m in formula (23) is about 3 to 6 and preferably about 4 to 6, and n is 2 or greater.

The value of n in formula (23) is a value such that the polyoxy $C_2$-$C_6$ alkylene glycol has an IOB of about 0.00-0.60, a melting point of about 45° C. or less and a water solubility of about 0.00-0.05 g in 100 g of water at 25° C.

For example, when formula (23) is polypropylene glycol (m=3, homopolymer), the IOB is 0.58 when n=12. Thus, when formula (23) is polypropylene glycol (m=3, homopolymer), the condition for the IOB is satisfied when m is equal to or greater than about 12.

Also, when formula (23) is polybutylene glycol (m=4, homopolymer), the IOB is 0.57 when n=7. Thus, when formula (23) is polybutylene glycol (m=4, homopolymer), the condition for the IOB is satisfied when n is equal to or greater than about 7.

From the viewpoint of IOB, melting point and water solubility, the weight-average molecular weight of the polyoxy $C_4$-$C_6$ alkylene glycol is preferably between about 200 and about 10,000, more preferably between about 250 and about 8,000, and even more preferably in the range of about 250 to about 5,000.

Also from the viewpoint of IOB, melting point and water solubility, the weight-average molecular weight of a polyoxy $C_3$ alkylene glycol, i.e. polypropylene glycol, is preferably between about 1,000 and about 10,000, more preferably between about 3,000 and about 8,000, and even more preferably between about 4,000 and about 5,000. This is because if the weight-average molecular weight is less than about 1,000, the condition for the water solubility will not be satisfied, and a larger weight-average molecular weight will particularly tend to increase the migration rate into the absorbent body and the whiteness of the top sheet.

Examples of commercial products of polyoxy $C_2$-$C_6$ alkylene glycols include UNIOL™ D-1000, D-1200, D-2000, D-3000, D-4000, PB-500, PB-700, PB-1000 and PB-2000 (all products of NOF Corp.).

[($e_2$) Ester of a Polyoxy $C_2$-$C_6$ Alkylene Glycol and at Least One Fatty Acid]

Examples of an ester of a polyoxy $C_2$-$C_6$ alkylene glycol and at least one fatty acids include the polyoxy $C_2$-$C_6$ alkylene glycols mentioned for "($e_1$) Polyoxy $C_2$-$C_6$ alkylene glycol" in which one or both OH ends have been esterified with fatty acids, i.e. monoesters and diesters.

Examples of fatty acids to be esterified in the ester of a polyoxy $C_2$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

An example of a commercially available ester of a polyoxy $C_2$-$C_6$ alkylene glycol and a fatty acid is WILBRITE cp9 (product of NOF Corp.).

[($e_3$) Ether of a Polyoxy $C_2$-$C_6$ Alkylene Glycol and at Least One Aliphatic Monohydric Alcohol]

Examples of an ether of a polyoxy $C_2$-$C_6$ alkylene glycols and at least one aliphatic monohydric alcohol include the polyoxy $C_2$-$C_6$ alkylene glycols mentioned for "($e_1$) Polyoxy $C_2$-$C_6$ alkylene glycol" wherein one or both OH ends have been etherified by an aliphatic monohydric alcohol, i.e. monoethers and diethers.

In an ether of a polyoxy $C_2$-$C_6$ alkylene glycol and at least one aliphatic monohydric alcohol, the aliphatic monohydric alcohol to be etherified may be an aliphatic monohydric alcohol among those mentioned for "compound (B)".

[($e_4$) Ester of a Polyoxy $C_2$-$C_6$ Alkylene Glycol and a Chain Hydrocarbon Tetracarboxylic Acid, Chain Hydrocarbon Tricarboxylic Acid or Chain Hydrocarbon Dicarboxylic Acid]

The polyoxy $C_2$-$C_6$ alkylene glycol to be esterified for the aforementioned ester of a polyoxy $C_2$-$C_6$ alkylene glycol and a chain hydrocarbon tetracarboxylic acid, chain hydrocarbon tricarboxylic acid or chain hydrocarbon dicarboxylic acid may be any of the polyoxy $C_2$-$C_6$ alkylene glycols mentioned above under "($e_1$) Polyoxy $C_2$-$C_6$ alkylene glycol". Also, the chain hydrocarbon tetracarboxylic acid, chain hydrocarbon tricarboxylic acid or chain hydrocarbon dicarboxylic acid to be esterified may be any of those mentioned above for "compound (C)".

The ester of a polyoxy $C_2$-$C_6$ alkylene glycol and a chain hydrocarbon tetracarboxylic acid, chain hydrocarbon tricarboxylic acid or chain hydrocarbon dicarboxylic acid may be a commercially available product, or it may be produced by polycondensation of a $C_2$-$C_6$ alkylene glycol with a chain hydrocarbon tetracarboxylic acid, chain hydrocarbon tricarboxylic acid or chain hydrocarbon dicarboxylic acid under known conditions.

[($e_5$) Ether of a Polyoxy $C_2$-$C_6$ Alkylene Glycol and a Chain Hydrocarbon Tetraol, Chain Hydrocarbon Triol or Chain Hydrocarbon Diol]

The polyoxy $C_2$-$C_6$ alkylene glycol to be etherified for the aforementioned ether of a polyoxy $C_2$-$C_6$ alkylene glycol and a chain hydrocarbon tetraol, chain hydrocarbon triol or chain hydrocarbon diol may be any of the polyoxy $C_2$-$C_6$ alkylene glycols mentioned above under "($e_1$) polyoxy $C_2$-$C_6$ alkylene glycol". Also, the chain hydrocarbon tetraol, chain hydrocarbon triol or chain hydrocarbon diol to be etherified may be, for example, pentaerythritol, glycerin or glycol, mentioned above for "compound (A)".

Examples of commercially available ethers of polyoxy $C_2$-$C_6$ alkylene glycols and chain hydrocarbon tetraols, chain hydrocarbon triols and chain hydrocarbon diols include UNILUBE™ 5 TP-300 KB and UNIOL™ TG-3000 and TG-4000 (products of NOF Corp.).

UNILUBE™ 5 TP-300 KB is a compound obtained by polycondensation of 65 mol of propylene glycol and 5 mol of ethylene glycol with 1 mol of pentaerythritol, and it has an IOB of 0.39, a melting point of below 45° C., and a water solubility of less than 0.05 g.

UNIOL™ TG-3000 is a compound obtained by polycondensation of 50 mol of propylene glycol with 1 mol of glycerin, and it has an IOB of 0.42, a melting point of below 45° C., a water solubility of less than 0.05 g, and a weight-average molecular weight of about 3,000.

UNIOL™ TG-4000 is a compound obtained by polycondensation of 70 mol of propylene glycol with 1 mol of glycerin, and it has an IOB of 0.40, a melting point of below 45° C., a water solubility of less than 0.05 g, and a weight-average molecular weight of about 4,000.

The ether of a polyoxy $C_2$-$C_6$ alkylene glycol and a chain hydrocarbon tetraol, chain hydrocarbon triol or chain hydrocarbon diol may also be produced by adding a $C_2$-$C_6$ alkylene oxide to a chain hydrocarbon tetraol, chain hydrocarbon triol or chain hydrocarbon diol under known conditions.

[(F) Chain hydrocarbon]

The chain hydrocarbon has an inorganic value of 0 and thus an IOB of 0.00, while the water solubility is also approximately 0 g, and therefore if the melting point is about 45° C. or less it may be included among the aforementioned blood modifying agents. Examples of such chain hydrocarbons include ($f_1$) a chain alkane, such as linear alkanes and branched alkanes, and linear alkanes generally include those with not more than 22 carbons, in consideration of a melting point of about 45° C. or less. In consideration of vapor pressure, they generally include those with 13 or more carbons. Branched alkanes generally include those with 22 or more carbons, since their melting points are often lower than linear alkanes, given the same number of carbon atoms.

Examples of commercially available hydrocarbon products include PARLEAM 6 (NOF Corp.).

The blood modifying agent has been found to have at least a function of lowering blood viscosity and surface tension, which will be considered in detail in the examples. Menstrual blood to be absorbed by the absorbent article, unlike ordinary blood, contains proteins of the endometrial wall, for example, which act to bind together blood cells so that the blood cells form a rouleau state. Menstrual blood which is to be absorbed by the absorbent article therefore tends to have high viscosity, and when the top sheet and second sheet are nonwoven fabrics or woven fabric, the menstrual blood becomes clogged between the fibers creating a residual sticky feel for the wearer, while the menstrual blood also diffuses on the surface of the top sheet and tends to leak.

The blood modifying agent which has an IOB of about 0.00 to 0.60 has high organicity and readily infiltrates between blood cells, and it therefore stabilizes the blood cells and can prevent formation of a rouleau structure by the blood cells. For example, with an absorbent article comprising an acrylic super-absorbent polymer, or SAP, absorption of menstrual blood is known to lead to covering of the SAP surface by rouleau-formed blood cells and inhibition of the absorption performance of the SAP, but presumably stabilization of the blood cells allows the absorption performance of the SAP to be exhibited more easily. In addition, the blood modifying agent which has high affinity with erythrocytes protects the erythrocyte membranes, and therefore may minimize destruction of the erythrocytes.

The weight-average molecular weight of the blood modifying agent is preferably about 2,000 or less, and more preferably about 1,000 or less. A high weight-average molecular weight will tend to result in high viscosity of the blood modifying agent, and it will be difficult to lower the viscosity of the blood modifying agent by heating, to a viscosity suitable for coating. As a result, it will sometimes be necessary to dilute the blood modifying agent with a solvent. In addition, if the weight-average molecular weight is higher, tack may result in the blood modifying agent itself, tending to create a feeling of unpleasantness for the wearer. In the following examples, the blood modifying agent was confirmed to have a mechanism of lowering the viscosity and surface tension of blood.

EXAMPLES

The invention will now be further explained by examples, with the understanding that the invention is not limited to the examples.

Example 1

(1) Preparation of Absorbent Body Materials A (A1 to A7)

Pulp (NB416 by Warehouser) and thermal bondable composite fibers A (hereunder referred to as "composite fibers A") were blended in mass ratios of 9:1 (A1), 8:2 (A2), 6.5:3.5 (A3), 5:5 (A4), 3.5:6.5 (A5), 2:8 (A6) and 0:10 (A7), to prepare absorbent body materials A1 to A7 (basis weight: 200 g/m$^2$).

The composite fibers A were core-sheath composite fibers having polyethylene terephthalate (PET) as a core component, and high-density polyethylene (HDPE), graft polymerized with a maleic anhydride-containing vinyl polymer, as a sheath component. The core-sheath ratio of the composite fibers A was 50:50 (mass ratio), the titanium oxide content of the core component was 0.7 mass %, the fineness was 2.2 dtex and the fiber length was 6 mm.

(2) Preparation of Absorbent Body Materials B (B1 to B9)

Pulp (NB416 by Warehouser) and thermal bondable composite fibers B (hereunder referred to as "composite fibers B") were blended in mass ratios of 9:1 (B1), 8.5:1.5 (B2), 8:2

(B3), 6.5:3.5 (B4), 5:5 (B5), 3.5:6.5 (B6), 2:8 (B7), 0:10 (B8) and 10:0 (B9), to prepare absorbent body materials B1 to B9 (basis weight: 200 g/m²).

The composite fibers B were core-sheath composite fibers having polyethylene terephthalate (PET) as a core component, and ordinary high-density polyethylene (HDPE) as a sheath component. The core-sheath ratio of the composite fibers B was 50:50 (mass ratio), the titanium oxide content of the core component was 0.7 mass %, the fineness was 2.2 dtex and the fiber length was 6 mm.

(3) Production of Absorbent Body Samples A (A1 to A7) and B (B1 to B9)

Absorbent body materials A1 to A7 and B1 to B9 were bonded by a common air-through method, and the composite fibers A and B were thermally bonded to prepare absorbent body samples A1 to A7 and B1 to B9. The heating temperature was 135° C., the airflow rate was 5 m/sec and the heating time was 20 seconds.

(4) Measurement of Maximum Tensile Strength

[Dry Maximum Tensile Strength (N/25 mm)]

A sample piece (150 mm length×25 mm width, 5) was mounted on a tensile tester (AG-1kNI by Shimadzu Corp.) under standard conditions (temperature: 20° C., humidity: 60%), with a grip spacing of 100 mm, a load (maximum point load) was applied at a pull rate of 100 mm/min until the sample piece was severed, and the maximum tensile strength per 25 mm width was measured in the lengthwise direction (MD direction) of the sample piece.

[Wet Maximum Tensile Strength (N/25 mm)]

A sample piece (150 mm length×25 mm width) was dipped in ion-exchanged water until it sank under its own weight, or the sample piece was immersed in water for 1 hour or longer, and then measurement was performed in the same manner as above (ISO 9073-3, JIS L 1913 6.3) to determine the maximum tensile strength per 25 mm width in the lengthwise direction (MD direction) of the sample piece.

The measurements of dry and wet maximum tensile strength in other examples were performed in the same manner as described above.

(5) Measurements of Basis Weight, Thickness and Density of an Absorbent Body Sample The density of an absorbent body sample was calculated by the following formula:

$$D(g/cm^3) = B(g/m^2)/T(mm) \times 10^{-3}$$

wherein D, B and T represent the density, basis weight and thickness of an absorbent body sample, respectively.

The basis weight (g/m²) of an absorbent body sample was measured in the following manner:

Three sample pieces each having a size of 100 mm×100 mm were cut out of an absorbent body sample. Under standard conditions (temperature: 23±2° C., relative humidity: 50±5%), the mass of each sample piece was measured using a direct-reading balance (Electronic Balance HF-300 manufactured by Kensei Co., Ltd). The mass per unit area (g/m³) of the absorbent body, which was calculated based on an average of the three measured values, was used as the basis weight of the absorbent body sample.

In the measurement of the basis weight of the absorbent body sample, measurement conditions other than those specified above were selected in accordance with ISO 9073-1 or JIS L 1913 6.2.

The thickness (mm) of an absorbent body sample was measured in the following manner:

Under standard conditions (temperature: 23±2° C., relative humidity: 50±5%), a constant pressure of 3 g/cm² was applied by a thickness gauge (Thickness Gauge FS-60DS manufactured by DAIEI KAGAKU SEIKI MFG. Co., Ltd, which has a measuring plane of 44 mm in diameter) to five different regions (each having a diameter of 44 mm) of an absorbent body. At 10 seconds after the pressurization, the thickness of each region was measured by the thickness gauge. The thickness of the absorbent body was calculated as an average of the five measured values.

The measurements of basis weight, thickness and density of an absorbent body sample in other examples were performed in the same manner as described above.

(6) Results and Observations

The measurement results are shown in Table 2.

TABLE 2

| | | Absorbent body materials | | | Properties after heat treatment | | | | | | |
|---|---|---|---|---|---|---|---|---|---|---|---|
| | | Pulp | Composite fiber | | Actual | | | Maximum tensile strength (N/25 mm) | | | |
| | | basis weight (g/m²) | basis weight (g/m²) | Mixing ratio (mass ratio) | basis weight (g/m²) | Thickness (mm) | Density (g/cm³) | Dry | Wet | Difference between Dry and Wet | WEB state |
| Absorbent body sample A | 1 | 180 | 20 | 9:1 | 210 | 8.92 | 0.0235 | 3.42 | 2.02 | 1.4 | 0.049 |
| | 2 | 160 | 40 | 8:2 | 197 | 8.76 | 0.0225 | 9.59 | 5.10 | 4.49 | 0.043 |
| | 3 | 130 | 70 | 6.5:3.5 | 206 | 9.53 | 0.0216 | 20.80 | 15.09 | 5.72 | 0.055 |
| | 4 | 100 | 100 | 5:5 | 215 | 9.27 | 0.0232 | 40.89 | 33.72 | 7.17 | 0.153 |
| | 5 | 70 | 130 | 3.5:6.5 | 219 | 8.54 | 0.0256 | 67.47 | 54.39 | 13.09 | 0.140 |
| | 6 | 40 | 160 | 2:8 | 223 | 6.87 | 0.0325 | 83.19 | 81.25 | 1.94 | 0.095 |
| | 7 | 0 | 200 | 0:10 | 222 | 6.47 | 0.0344 | 133.64 | 129.06 | 4.58 | 0.060 |
| Absorbent body sample B | 1 | 180 | 20 | 9:1 | 205 | 8.66 | 0.0237 | 0.46 | 0.35 | 0.11 | 0.032 |
| | 2 | 170 | 30 | 8.5:1.5 | 202 | 8.39 | 0.0241 | 1.11 | 1.02 | 0.09 | 0.027 |
| | 3 | 160 | 40 | 8:2 | 206 | 8.21 | 0.0251 | 2.33 | 2.04 | 0.30 | 0.190 |
| | 4 | 130 | 70 | 6.5:3.5 | 215 | 9.07 | 0.0237 | 7.58 | 6.69 | 0.89 | 0.150 |
| | 5 | 100 | 100 | 5:5 | 214 | 9.02 | 0.0237 | 15.70 | 14.70 | 1.00 | 0.025 |
| | 6 | 70 | 130 | 3.5:6.5 | 222 | 9.07 | 0.0245 | 27.89 | 25.62 | 2.27 | 0.033 |
| | 7 | 40 | 160 | 2:8 | 223 | 7.97 | 0.0280 | 41.52 | 37.88 | 3.64 | 0.017 |
| | 8 | 0 | 200 | 0:10 | 218 | 5.63 | 0.0387 | 67.23 | 61.76 | 5.47 | 0.038 |
| | 9 | 200 | 0 | 10:0 | — | — | — | 0.375 | 0.01 | 0.37 | 0.375 |

The following observations are made based on Table 2.

For absorbent body sample A, if a mixing ratio (mass ratio) of the composite fibers A to the pulp is lower than 1/9, this is expected to result in a wet maximum tensile strength of less than 2 N/25 mm, potentially making it impossible to guarantee strength when wet. From the viewpoint of ensuring strength for absorbent body sample A, therefore, it is believed that the mixing ratio (mass ratio) of the composite fibers A to the pulp must be at least 1/9.

For absorbent body sample B, if a mixing ratio (mass ratio) of the composite fibers B to the pulp is 1.5/8.5 or less, this results in a wet maximum tensile strength of less than 2 N/25 mm, making it impossible to guarantee strength when wet. From the viewpoint of ensuring strength for absorbent body sample B, therefore, it is believed that the mixing ratio (mass ratio) of the composite fibers B to the pulp must be greater than 1.5/8.5.

Upon comparing absorbent body samples with identical mixing ratios (mass ratios) of the pulp and the composite fibers A, B (for example, absorbent body sample A1 and absorbent body sample B1), the maximum tensile strengths (dry and wet) are found to be larger with absorbent body sample A than with absorbent body sample B, for all of mixing ratios (mass ratios). Also, when the mixing ratio (mass ratio) of the pulp and composite fibers A, B is in the range of 9:1 to 3.5:6.5 (absorbent body samples A1 to A5 and B1 to B6), the difference between the dry maximum tensile strength and the wet maximum tensile strength (dry maximum tensile strength—wet maximum tensile strength) is larger with absorbent body sample A than with absorbent body sample B.

This difference in strength is attributed to the fact that with absorbent body sample A, hydrogen bonds are formed between the oxygen atoms of acyl group and ether bond of maleic anhydride and the OH groups of cellulose, whereas such hydrogen bonds are not formed with absorbent body sample B.

This is also supported by the maximum tensile strength of each sample in a web state. In other words, the maximum tensile strengths of the samples in the web state were measured to be less than 0.4 N/25 mm for all of the samples (see Table 2), suggesting that the difference in strength is due not to differences in the degree of entangling but rather to the presence or absence of hydrogen bond formation. The sample in the web state is a sample without any treatment after layering of the absorbent body material on the base material, and it has not been subjected to any treatment including entangling treatment such as needle punching, heat treatment such as hot air, embossing, energy waves or the like, or adhesive treatment.

Also, as shown in Table 3 below, since the composite fibers A have a larger heat of fusion than the composite fibers B, the composite fibers A have a higher degree of crystallinity than the composite fibers B, and therefore the difference in strength is believed to be due to the difference in the degrees of crystallinity of the composite fibers A, B (the bonding strength between the fibers themselves).

TABLE 3

| | | Tim (° C.) | Tpm (° C.) | ΔH (J/g) |
|---|---|---|---|---|
| | | First heating | | |
| Thermal bondable composite fiber | A | 128/213.6 | 131.0/200.3 | 125.7/34.3 |
| | B | 125.6/249.0 | 128.3/251.4 | 86.9/27.6 |

TABLE 3-continued

| | | Tim (° C.) | Tpm (° C.) | ΔH (J/g) |
|---|---|---|---|---|
| | | Second heating | | |
| Thermal bondable composite fiber | A | 123.9/239.2 | 129.8/254.6 | 129.7/28.1 |
| | B | 122.8/241.8 | 129.1/253.6 | 96.5/18.4 |

Incidentally, although Japanese Unexamined Patent Publication No. 2004-270041 teaches that with a maleic anhydride graft-polymerized modified polyolefin, the carboxylic acid anhydride groups of the maleic anhydride are split and form covalent bonds with hydroxyl groups on the cellulose fiber surfaces, and that adhesion with the cellulose fibers is satisfactory, no increase in strength due to formation of covalent bonds was observed in this result.

Example 2

(1) Production of Absorbent Body Samples C (C1 to C7) and D (D1 to D9)

A carrier sheet (tissue basis weight: 14 g/m², product of UCKN) was mounted on each of absorbent body materials A1 to A7 (see Example 1) and bonded by a common air-through method, and after thermal fusion bonding of composite fibers A (heating temperature: 135° C., airflow rate: 5 m/sec, heating time: 20 sec), the density was adjusted to approximately 0.08 g/cm³ (0.0793-0.0817 g/cm³) with a steam jet (SJ) belt press machine, to produce absorbent body samples C1 to C7 (120 mm×120 mm, 3 samples each).

Absorbent body materials B1 to B9 (see Example 1) were used to produce absorbent body samples D1 to D9 (120 mm×120 mm, 3 samples each), in the same manner.

Figure 8:
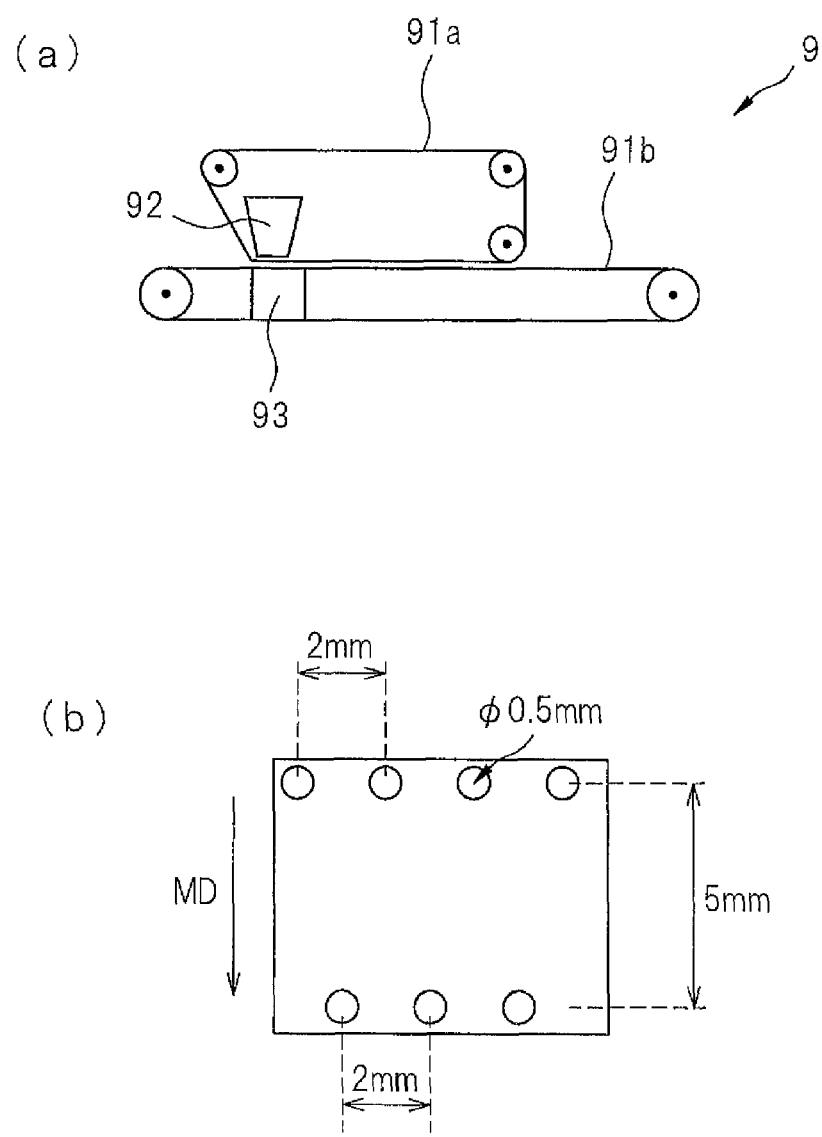
FIGS. 8(a) and (b) are diagrams showing an SJ belt press machine as used in the examples.

The construction of the SJ belt press machine used is illustrated in FIG. 8.

As shown in FIG. 8(a), the SJ belt press machine 9 comprises mesh conveyor belts 91a, 91b, a steam nozzle 92 and a suction box 93, and an absorbent body sandwiched between the pair of mesh conveyor belts 91a, 91b is transported between a mutually opposing steam nozzle 92 and suction box 93, injecting high-pressure steam toward the absorbent body through the steam nozzle 92, thereby compacting the absorbent body. The water vapor that has passed through the absorbent body is aspirated by the suction box 93 and ejected. The thickness of the absorbent body can be adjusted by varying the spacing between the pair of mesh conveyor belts 91a, 91b.

The mesh conveyor belts 91a, 91b are plain weave mesh conveyors made of polyphenylene sulfide (product of Nippon Filcon Co., Ltd.), having a longitudinal/transverse line size of 0.37 mm, with 34 longitudinal lines/inch and 32 transverse lines/inch. The distance between the mesh conveyor belts 91a, 91b was adjusted to 1 mm or 0.2 mm, and the line speed was 200 m/sec.

The steam nozzle 92 had 0.5 mm caliber open holes formed with a hole pitch of 2 mm/5 mm, as shown in FIG. 8(b), the vapor pressure of the injected water vapor was 0.7 MPa, and the steam treatment volume was 1.27 kg/m² per unit area.

(2) Measurement of Absorption Property (Penetration Time, Liquid Drain Time)

A top sheet (top sheet of Sofy Hadaomoi (trade name)) was placed on each absorbent body sample piece, and a perforated acrylic board (40 mm×10 mm hole at the center, 200 mm (length)×100 mm (width)) was layered over it. An autoburette (MultiDosimat Model E725-1 manufactured by SIBATA SCIENTIFIC TECHNOLOGY LTD.) was used to inject 3 ml of artificial menstrual blood (a mixture of 80 g glycerin, 8 g carboxymethyl cellulose sodium, 10 g sodium chloride, 4 g sodium hydrogencarbonate, 8 g Food Red No. 102, 2 g Food Red No. 2 and 2 g Food Yellow No. 5 thoroughly stirred with 1 L of ion-exchanged water) toward the hole of the acrylic board at 90 ml/min. The time from the start of injection until the artificial menstrual blood pooled in the acrylic board hole disappeared was recorded as the penetration time (sec), and the time from the start of injection until the artificial menstrual blood disappeared from the top sheet interior was recorded as the drain time (sec).

(3) Measurement of Dry and Wet Maximum Tensile Strengths

The dry and wet maximum tensile strengths for each absorbent body sample piece were measured in the same manner as Example 1.

(4) Results and Observations

The measurement results are shown in Table 4.

strength of less than 2 N/25 mm, making it impossible to guarantee strength when wet. From the viewpoint of ensuring strength for absorbent body sample D, therefore, it is believed that the mixing ratio (mass ratio) of the composite fibers B to the pulp must be greater than 1.5/8.5.

Based on the results shown in Table 4, it has been demonstrated that when the absorbent body density is approximately 0.08 g/cm$^3$ (0.0793-0.0817 g/cm$^3$), the absorbent body has both sufficient strength and absorption properties if the mixing ratio (mass ratio) of the pulp to the composite fibers A is in the range of 9:1 to 5:5. This is because the composite fibers A can guarantee strength for the absorbent body even when present in a smaller amount than the composite fibers B (and thus avoids inhibiting the absorption property).

TABLE 4

| | | Absorbent body materials | | | Properties | | | | | | |
| | | Pulp | Composite fiber | | after density adjustment | | | Maximum tensile strength | | | Surface |
| | | | | | Actual | | | (N/25 mm) | | | |
| | | basis weight (g/m$^2$) | basis weight (g/m$^2$) | Mixing ratio (mass ratio) | basis weight (g/m$^2$) | Thickness (mm) | Density (g/cm$^3$) | Dry | Wet | Difference between Dry and Wet | Permeation speed (sec) | drain speed (sec) |
|---|---|---|---|---|---|---|---|---|---|---|---|---|
| Absorbent body sample C | 1 | 180 | 20 | 9:1 | 210 | 2.63 | 0.0798 | 3.69 | 2.17 | 1.52 | 4.54 | 15.34 |
| | 2 | 160 | 40 | 8:2 | 197 | 2.46 | 0.0801 | 8.9 | 5.77 | 3.13 | 4.84 | 17.22 |
| | 3 | 130 | 70 | 6.5:3.5 | 206 | 2.55 | 0.0808 | 19.37 | 14.75 | 4.62 | 5.52 | 17.95 |
| | 4 | 100 | 100 | 5:5 | 215 | 2.71 | 0.0793 | 35.59 | 31.03 | 4.56 | 5.27 | 31.18 |
| | 5 | 70 | 130 | 3.5:6.5 | 219 | 2.74 | 0.0799 | 63.22 | 49.36 | 13.86 | 7.73 | ≥300 |
| | 6 | 40 | 160 | 2:8 | 223 | 2.79 | 0.0799 | 81.11 | 79.36 | 1.75 | 10.03 | ≥300 |
| | 7 | 0 | 200 | 0:10 | 222 | 2.77 | 0.0801 | 130.39 | 125.94 | 4.45 | 10.33 | ≥300 |
| Absorbent body sample D | 1 | 180 | 20 | 9:1 | 205 | 2.54 | 0.0807 | 0.77 | 0.57 | 0.20 | 4.59 | 16.87 |
| | 2 | 170 | 30 | 8.5:1.5 | 202 | 2.48 | 0.0815 | 2.19 | 1.94 | 0.25 | 4.60 | 17.15 |
| | 3 | 160 | 40 | 8:2 | 206 | 2.52 | 0.0817 | 3.67 | 3.08 | 0.59 | 4.89 | 30.98 |
| | 4 | 130 | 70 | 6.5:3.5 | 215 | 2.63 | 0.0817 | 8.24 | 7.34 | 0.90 | 5.28 | 40.56 |
| | 5 | 100 | 100 | 5:5 | 214 | 2.63 | 0.0814 | 17.6 | 16.3 | 1.30 | 8.25 | ≥300 |
| | 6 | 70 | 130 | 3.5:6.5 | 222 | 2.73 | 0.0813 | 29.31 | 27.25 | 2.06 | 9.13 | ≥300 |
| | 7 | 40 | 160 | 2:8 | 223 | 2.76 | 0.0808 | 43.73 | 40.10 | 3.63 | 9.82 | ≥300 |
| | 8 | 0 | 200 | 0:10 | 218 | 2.74 | 0.0796 | 68.66 | 62.36 | 6.30 | 4.33 | 14.82 |
| | 9 | 200 | 0 | 10:0 | — | — | — | 0.375 | 0.01 | 0.37 | — | — |

As seen in Table 4, when the mixing ratio (mass ratio) of the pulp to the composite fibers A was in the range of 9:1 to 5:5 (absorbent body samples C1 to C4), the absorption property of the absorbent body sample was adequate, but when the mixing ratio (mass ratio) of the pulp to the composite fibers A was in the range of 3.5:6.5 to 0:10 (absorbent body samples C5 to C7), the absorption property of the absorbent body sample was significantly reduced.

Also as seen in Table 4, for absorbent body sample C, if a mixing ratio (mass ratio) of the composite fibers A to the pulp is lower than 1/9, this is expected to result in a wet maximum tensile strength of less than 2 N/25 mm, which may make it impossible to guarantee strength when wet. From the viewpoint of ensuring strength for absorbent body sample C, therefore, it is believed that the mixing ratio (mass ratio) of the composite fibers A to the pulp must be at least 1/9.

Also as seen in Table 4, for absorbent body sample D, if a mixing ratio (mass ratio) of the composite fibers B to the pulp is 1.5/8.5 or less, this results in a wet maximum tensile Example 3

The optimal range for the mixing ratio (mass ratio) of the pulp to the composite fibers A was investigated from the viewpoint of strength and absorption property, for a system according to Example 2, with the density fixed at approximately 0.08 g/cm$^3$ (0.0793-0.0817 g/cm$^3$).

In this example, the optimal range for the density was investigated from the viewpoint of the absorption property.

Using a blend of pulp (NB416 by Warehouser) and composite fibers A in the mixing ratio (mass ratio) shown in Table 5 (basis weight: 200 g/m$^2$), absorbent body samples E1 to E9 were produced with different densities (0.05, 0.06, 0.07, 0.08, 0.09, 0.1, 0.12, 0.13, 0.14 g/cm$^3$), and their absorption properties (liquid drain times) measured, in the same manner as Example 2.

The measurement results are shown in Table 5.

TABLE 5

|  |  | Pulp:Composite fiber | Density (g/cm³) | | | | | | | | |
| --- | --- | --- | --- | --- | --- | --- | --- | --- | --- | --- | --- |
|  |  |  | 0.05 | 0.06 | 0.07 | 0.08 | 0.09 | 0.1 | 0.12 | 0.13 | 0.14 |
| Absorbent body sample E | 1 | 9:1 | 300 | 32.91 | 21.22 | 16.55 | 16.73 | 16.89 | 19.64 | 25 | 27 |
|  | 2 | 8:2 | 300 | 36.98 | 23.06 | 17.05 | 17.22 | 17.82 | 21.29 | 29 | 32 |
|  | 3 | 6.5:3.5 | 300 | 40.75 | 25.31 | 17.58 | 17.95 | 19.45 | 25.28 | 49.3 | 55.19 |
|  | 4 | 5:5 | 300 | 50.81 | 35.46 | 30.79 | 31.18 | 45.66 | 58.36 | 70 | 85 |
|  | 5 | 4:6 | 300 | 250 | 250 | 250 | 250 | 250 | 250 | 300 | 300 |
|  | 6 | 3.5:6.5 | 300 | 300 | 300 | 300 | 300 | 300 | 300 | 300 | 300 |
|  | 7 | 2:8 | 300 | 300 | 300 | 300 | 300 | 300 | 300 | 300 | 300 |
|  | 8 | 0:10 | 300 | 300 | 300 | 300 | 300 | 300 | 300 | 300 | 300 |
|  | 9 | 10:0 | 250 | 20.33 | 15.11 | 14.72 | 14.82 | 15.21 | 14.53 | 13.77 | 15.48 |

The following conclusions were drawn from the measurement results shown in Table 5.

When the mixing ratio (mass ratio) of the pulp to the composite fibers A is in the range of 9:1 to 5:5, the density range which demonstrates sufficient liquid drain performance (specifically, the liquid drain time after dropping 3 cc of artificial menstrual blood is within 90 seconds) is 0.06 to 0.14 g/cm³.

If the density is below 0.06 g/cm³, the liquid drain time exceeds 90 seconds for all mixing ratios. It is believed that when the density is below 0.06 g/cm³, the distance between fibers increases and capillary force no longer acts.

If the density is greater than 0.12 g/cm³, the mixing ratio (mass ratio) of the pulp to the composite fibers A in the range of 9:1 to 6.5:3.5 results in the liquid drain time of 60 seconds or less, whereas the mixing ratio outside of this rage results in more than 60 seconds. If the density is greater than 0.12 g/cm³, capillary action will take place but the liquid mobility space will decrease, resulting in increased resistance to liquid mobility and thus reduced liquid drain performance.

The results for Examples 1 to 3 demonstrated that the optimal range for the mixing ratio (mass ratio) of the pulp to the composite fibers A is between 9:1 and 5:5, and that the optimal density is 0.06 to 0.14 g/cm³.

Example 4

In this example it was confirmed that the blood modifying agent lowers the viscosity and surface tension of menstrual blood and allows menstrual blood to rapidly migrate from the top sheet into the absorbent body.

Example 4-1

[Data of Blood Modifying Agents]

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m²), a second sheet, formed of an air-through nonwoven fabric (composite fiber composed of polyester and polyethylene terephthalate, basis weight: 30 g/m²), an absorbent body comprising pulp (basis weight: 150-450 g/m², increased at the center section), an acrylic super-absorbent polymer (basis weight: 15 g/m²) and tissue as a core wrap, a water-repellent agent-treated side sheet, and a back sheet composed of a polyethylene film.

The blood modifying agents used for testing are listed below.

[($a_1$) Ester of a Chain Hydrocarbon Tetraols and at Least One Fatty Acid]

UNISTAR H-408BRS, product of NOF Corp.
Pentaerythritol tetra(2-ethylhexanoate), weight-average molecular weight: approximately 640

UNISTAR H-2408BRS-22, product of NOF Corp.
Mixture of pentaerythritol tetra(2-ethylhexanoate) and neopentylglycol di(2-ethylhexanoate) (58:42 as weight ratio), weight-average molecular weight: approximately 520

[($a_2$) Ester of a Chain Hydrocarbon Triols and at Least One Fatty Acid]

Cetiol SB45DEO, Cognis Japan
Glycerin and fatty acid triester, with oleic acid or stearylic acid as the fatty acid.

SOY42, product of NOF Corp.
Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L oil fatty acid glyceride, product of NOF Corp.
Glycerin and fatty acid triester with $C_8$ fatty acid:$C_{10}$ fatty acid:$C_{12}$ fatty acid at a mass ratio of about 37:7:56, weight-average molecular weight: approximately 570

Tri-CL oil fatty acid glyceride, product of NOF Corp.
Glycerin and fatty acid triester with $C_8$ fatty acid:$C_{12}$ fatty acid at a mass ratio of about 44:56, weight-average molecular weight: approximately 570

PANACET 810s, product of NOF Corp.
Glycerin and fatty acid triester with $C_8$ fatty acid:$C_{10}$ fatty acid at a mass ratio of about 85:15, weight-average molecular weight: approximately 480

PANACET 800, product of NOF Corp.
Glycerin and fatty acid triester with octanoic acid ($C_8$) as the entire fatty acid portion, weight-average molecular weight: approximately 470

PANACET 800B, product of NOF Corp.
Glycerin and fatty acid triester with 2-ethylhexanoic acid ($C_8$) as the entire fatty acid portion, weight-average molecular weight: approximately 470

NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut fatty acid glyceride, product of NOF Corp.
Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670

Caprylic acid diglyceride, product of NOF Corp.
Glycerin and fatty acid diester with octanoic acid as the fatty acid, weight-average molecular weight: approximately 340

[(a₃) Ester of a Chain Hydrocarbon Diol and at Least One Fatty Acid]

COMPOL BL, product of NOF Corp.
Dodecanoic acid ($C_{12}$) monoester of butylene glycol, weight-average molecular weight: approximately 270
COMPOL BS, product of NOF Corp.
Octadecanoic acid ($C_{18}$) monoester of butylene glycol, weight-average molecular weight: approximately 350
UNISTAR H-208BRS, product of NOF Corp.
Neopentyl glycol di(2-ethylhexanoate), weight-average molecular weight: approximately 360

[(c₂) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-acetylcitrate, product of Tokyo Kasei Kogyo Co., Ltd.
Weight-average molecular weight: approximately 400

[(c₃) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl adipate, product of Wako Pure Chemical Industries, Ltd.
Weight-average molecular weight: approximately 380

[(d₃) Ester of a Fatty Acid and an Aliphatic Monohydric Alcohol]

ELECTOL WE20, product of NOF Corp.
Ester of dodecanoic acid ($C_{12}$) and dodecyl alcohol ($C_{12}$), weight-average molecular weight: approximately 360
ELECTOL WE40, product of NOF Corp.
Ester of tetradecanoic acid ($C_{14}$) and dodecyl alcohol ($C_{12}$), weight-average molecular weight: approximately 390

[(e₁) Polyoxy $C_2$-$C_6$ Alkylene Glycol]

UNIOL D-1000, product of NOF Corp.
Polypropylene glycol, weight-average molecular weight: approximately 1,000
UNIOL D-1200, product of NOF Corp.
Polypropylene glycol, weight-average molecular weight: approximately 1,200
UNIOL D-3000, product of NOF Corp.
Polypropylene glycol, weight-average molecular weight: approximately 3,000
UNIOL D-4000, product of NOF Corp.
Polypropylene glycol, weight-average molecular weight: approximately 4,000
UNIOL PB500, product of NOF Corp.
Polybutylene glycol, weight-average molecular weight: approximately 500
UNIOL PB700, product of NOF Corp.
Polyoxybutylene polyoxypropylene glycol, weight-average molecular weight: approximately 700
UNIOL PB1000R, product of NOF Corp.
Polybutylene glycol, weight-average molecular weight: approximately 1000

[(e₂) Ester of a Polyoxy $C_2$-$C_6$ Alkylene Glycol and at Least One Fatty Acid]

WILBRITE cp9, product of NOF Corp.
Polybutylene glycol compound with OH groups at both ends esterified by hexadecanoic acid ($C_{16}$), weight-average molecular weight: approximately 1,150

[(e₃) Ether of a Polyoxy $C_2$-$C_6$ Alkylene Glycol and at Least One Aliphatic Monohydric Alcohol]

UNILUBE MS-70K, product of NOF Corp.
Stearyl ether of polypropylene glycol, approximately 15 repeating units, weight-average molecular weight: approximately 1,140

[(e₅) Ethers of a Polyoxy $C_2$-$C_6$ Alkylene Glycol and a Chain Hydrocarbon Tetraol, Chain Hydrocarbon Triol or Chain Hydrocarbon Diol]

UNILUBE 5TP-300 KB
Polyoxyethylenepolyoxypropylene pentaerythritol ether, produced by addition of 5 mol of ethylene oxide and 65 mol of propylene oxide to 1 mol of pentaerythritol, weight-average molecular weight: 4,130
UNIOL TG-3000, product of NOF Corp.
Glyceryl ether of polypropylene glycol, approximately 16 repeating units, weight-average molecular weight: approximately 3,000
UNIOL TG-4000, product of NOF Corp.
Glyceryl ether of polypropylene glycol, approximately 16 repeating units, weight-average molecular weight: approximately 4,000

[(f₁) Chain Alkane]

PARLEAM 6, product of NOF Corp.
Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.
Glycerin and fatty acid triester obtained by addition of hydrogen to NA36 for reduced proportion of double bonds from unsaturated fatty acid starting material, weight-average molecular weight: approximately 880
(Caprylic acid/capric acid) monoglyceride, product of NOF Corp.
Glycerin and fatty acid monoester, with octanoic acid ($C_8$) and decanoic acid ($C_{10}$) at a mass ratio of about 85:15, weight-average molecular weight: approximately 220
Monomuls 90-L2 lauric acid monoglyceride, product of Cognis Japan
Isopropyl citrate, product of Tokyo Kasei Kogyo Co., Ltd.
Weight-average molecular weight: approximately 230
Diisostearyl malate
Weight-average molecular weight: approximately 640
UNIOL D-400, product of NOF Corp.
Polypropylene glycol, weight-average molecular weight: approximately 400
PEG1500, product of NOF Corp.
Polyethylene glycol, weight-average molecular weight: approximately 1,500-1,600
NONION S-6, product of NOF Corp.
Polyoxyethylene monostearate, approximately 7 repeating units, weight-average molecular weight: approximately 880
WILBRITE s753, product of NOF Corp.
Polyoxyethylene polyoxypropylene polyoxybutylene glycerin, weight-average molecular weight: approximately 960
UNIOL TG-330, product of NOF Corp.
Glyceryl ether of polypropylene glycol, approximately 6 repeating units, weight-average molecular weight: approximately 330
UNIOL TG-1000, product of NOF Corp.
Glyceryl ether of polypropylene glycol, approximately 16 repeating units, weight-average molecular weight: approximately 1,000
UNILUBE DGP-700, product of NOF Corp.
Diglyceryl ether of polypropylene glycol, approximately 9 repeating units, weight-average molecular weight: approximately 700
UNIOX HC60, product of NOF Corp.
Polyoxyethylene hydrogenated castor oil, weight-average molecular weight: approximately 3,570

Vaseline, product of Cognis Japan
Petroleum-derived hydrocarbon, semi-solid

The IOBs, melting points and water solubilities of the samples are shown in Table 6.

The water solubility was measured by the method described above, and samples that dissolved 24 hours after addition of 20.0 g to 100 g of desalted water were evaluated as "20 g<", and samples of which 0.05 g dissolved in 100 g of desalted water but 1.00 g did not dissolve were evaluated as 0.05-1.00 g.

For the melting point, "<45" indicates a melting point of below 45° C.

The skin contact surface of the top sheet of the sanitary napkin was coated with the aforementioned blood modifying agent. Each blood modifying agent was used directly, when the blood modifying agent was liquid at room temperature, or when the blood modifying agent was solid at room temperature it was heated to its melting point +20° C., and a control seam HMA gun was used for atomization of the blood modifying agent and coating onto the entire skin contact surface of the top sheet to a basis weight of about 5 g/m².

Figure 9:
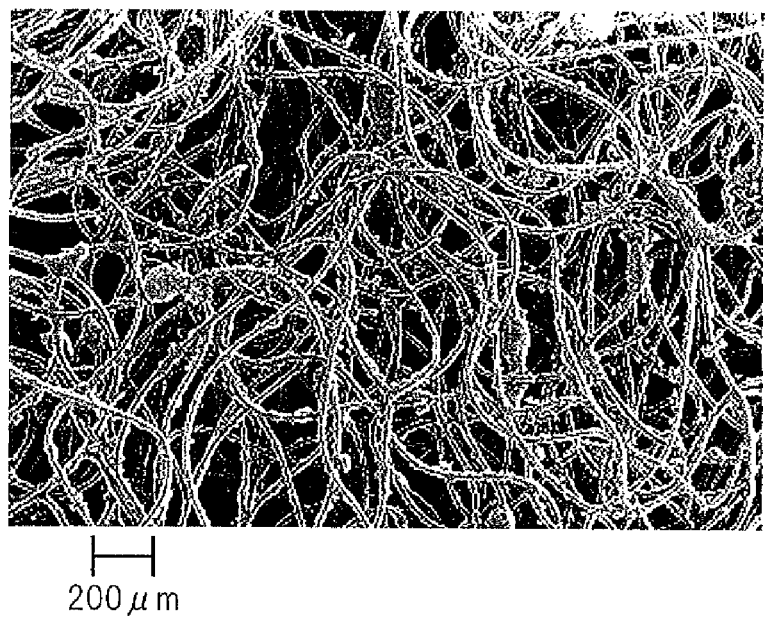
FIG. 9 is an electron micrograph of the skin contact surface of a top sheet in a sanitary napkin wherein the top sheet comprises a tri-C2L oil fatty acid glyceride.

FIG. 9 is an electron micrograph of the skin contact surface of a top sheet in a sanitary napkin (No. 2-5) wherein the top sheet comprises tri-C2L oil fatty acid glycerides. As clearly seen in FIG. 9, the tri-C2L oil fatty acid glycerides are adhering onto the fiber surfaces as fine particulates.

The rewetting rate and absorbent body migration rate were measured by the procedure described above. The results are shown in Table 6 below.

[Test Methods]

An acrylic board with an opened hole (200 mm×100 mm, 125 g, with a 40 mm×10 mm hole opened at the center) was placed on a top sheet comprising each blood modifying agent, and 3.0 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3.0 g of horse EDTA blood at 37±1° C. was again added dropwise through the acrylic board hole with a pipette (twice).

After the second dropping of blood, the acrylic board was immediately removed and 10 sheets of filter paper (Advantec Toyo Kaisha, Ltd, Qualitative Filter Paper No. 2, 50 mm×35 mm, total mass of the 10 sheets of filter paper: $FW_0$ (g)) were placed on the location where the blood had been dropped, and then a weight was placed thereover to a pressure of 30 g/cm². After 1 minute, the filter paper was removed, total mass of 10 sheets of filter paper ($FW_1$ (g)) was measured, and the "rewetting rate" was calculated by the following formula.

$$\text{Rewetting rate (mass \%)} = 100 \times [FW_1(g) - FW_0(g)]/6.0 \text{ (g)}$$

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 6.

Next, the whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The results are summarized in Table 6.

TABLE 6

| No. | Type | Blood modifying agent Product name | IOB | Melting pt. (° C.) | Water solubility (g) | Weight-average mol. wt. | Rewetting rate (%) | Absorbent body migration rate (sec) | Top sheet whiteness |
|---|---|---|---|---|---|---|---|---|---|
| 2-1 | (a₁) | H-408BRS | 0.13 | <−5 | <0.05 | 640 | 1.2 | 3 | VG |
| 2-2 | | H-2408BRS-22 | 0.18 | <−5 | <0.05 | 520 | 2.0 | 3 | VG |
| 2-3 | (a₂) | Cetiol SB45DEO | 0.16 | 44 | <0.05 | | 7.0 | 6 | VG |
| 2-4 | | SOY42 | 0.16 | 43 | <0.05 | 880 | 5.8 | 8 | VG |
| 2-5 | | Tri C2L oil fatty acid glyceride | 0.27 | 37 | <0.05 | 570 | 0.3 | 3 | VG |
| 2-6 | | Tri CL oil fatty acid glyceride | 0.28 | 38 | <0.05 | 570 | 1.7 | 3 | VG |
| 2-7 | | PANACET 810s | 0.32 | −5 | <0.05 | 480 | 2.8 | 3 | VG |
| 2-8 | | PANACET 800 | 0.33 | −5 | <0.05 | 470 | 0.3 | 3 | VG |
| 2-9 | | PANACET 800B | 0.33 | −5 | <0.05 | 470 | 2.0 | 3 | VG |
| 2-10 | | NA36 | 0.16 | 37 | <0.05 | 880 | 3.9 | 5 | VG |
| 2-11 | | Tri-coconut fatty acid glyceride | 0.28 | 30 | <0.05 | 670 | 4.3 | 5 | VG |
| 2-12 | | Caprylic diglyceride | 0.58 | <45 | <0.05 | 340 | 4.2 | 9 | G |
| 2-13 | (a₃) | COMPOL BL | 0.50 | 2 | <0.05 | 270 | 2.0 | 5 | G |
| 2-14 | | COMPOL BS | 0.36 | 37 | <0.05 | 350 | 7.9 | 9 | G |
| 2-15 | | H-208BRS | 0.24 | <−5 | <0.05 | 360 | 2.0 | 5 | VG |
| 2-16 | (c₂) | Tributyl O-acetylcitrate | 0.60 | <45 | <0.05 | 400 | 6.2 | 8 | VG |
| 2-17 | (c₃) | Dioctyl adipate | 0.27 | <45 | <0.05 | 380 | 1.7 | 6 | VG |
| 2-18 | (d₃) | ELECTOL WE20 | 0.13 | 29 | <0.05 | 360 | 1.8 | 5 | VG |
| 2-19 | | ELECTOL WE40 | 0.12 | 37 | <0.05 | 390 | 1.8 | 4 | VG |
| 2-20 | (e₁) | UNIOL D-1000 | 0.51 | <45 | <0.05 | 1,000 | 6.8 | 15 | F |
| 2-21 | | UNIOL D-1200 | 0.48 | <45 | <0.05 | 1,160 | 0.5 | 11 | F |
| 2-22 | | UNIOL D-3000 | 0.39 | <45 | <0.05 | 3,000 | 1.7 | 10 | F |
| 2-23 | | UNIOL D-4000 | 0.38 | <45 | <0.05 | 4,000 | 1.0 | 7 | G |
| 2-24 | (e₁) | UNIOL PB500 | 0.44 | <45 | <0.05 | 500 | 4.5 | 4 | G |
| 2-25 | | UNIOL PB700 | 0.49 | −5 | <0.05 | 700 | 2.8 | 5 | G |
| 2-26 | | UNIOL PB1000R | 0.40 | <45 | <0.05 | 1,000 | 4.0 | 4 | G |
| 2-27 | (e₂) | WILBRITE cp9 | 0.21 | 35 | <0.05 | 1,150 | 1.4 | 3 | G |
| 2-28 | (e₃) | UNILUBE MS-70K | 0.30 | <−10 | <0.05 | 1,140 | 6.7 | 3 | G |

TABLE 6-continued

| No. | Type | Blood modifying agent Product name | IOB | Melting pt. (° C.) | Water solubility (g) | Weight-average mol. wt. | Rewetting rate (%) | Absorbent body migration rate (sec) | Top sheet whiteness |
|---|---|---|---|---|---|---|---|---|---|
| 2-29 | ($e_5$) | UNILUBE 5TP-300KB | 0.39 | <45 | <0.05 | 4,130 | 2.0 | 6 | G |
| 2-30 | | UNIOL TG-3000 | 0.42 | <45 | <0.05 | 3,000 | 0.8 | 6 | G |
| 2-31 | | UNIOL TG-4000 | 0.40 | <45 | <0.05 | 4,000 | 2.0 | 6 | G |
| 2-32 | ($f_1$) | PARLEAM 6 | 0.00 | −5 | <0.05 | 330 | 6.0 | 8 | VG |
| 2-33 | | NA50 | 0.18 | 52 | <0.05 | 880 | 15.5 | 60 | P |
| 2-34 | | (Caprylic/capric)monoglyceride | 1.15 | <45 | 20< | 220 | 4.0 | 4 | P |
| 2-35 | | 90-L2 Lauric acid monoglyceride | 0.87 | 58 | 20< | | 6.2 | 7 | P |
| 2-36 | | Isopropyl citrate | 1.56 | <45 | 20< | 230 | 12.2 | 5 | G |
| 2-37 | | Diisostearyl malate | 0.28 | <45 | 20< | 640 | 5.5 | 8 | F |
| 2-38 | | UNIOL D-400 | 0.76 | <45 | 0.05< | 400 | 8.7 | 40 | P |
| 2-39 | | PEG1500 | 0.78 | 40 | 20< | 1,500-1,600 | 11.0 | 38 | P |
| 2-40 | | NONION S-6 | 0.44 | 37 | 0.05< | 880 | 8.4 | 7 | P |
| 2-41 | | WILBRITE s753 | 0.67 | −5 | 20< | 960 | 9.3 | 9 | F |
| 2-42 | | UNIOL TG-330 | 1.27 | <45 | 0.05< | 330 | — | — | — |
| 2-43 | | UNIOL TG-1000 | 0.61 | <45 | <0.05 | 1,000 | 14.2 | 7 | G |
| 2-44 | | UNILUBE DGP-700 | 0.91 | <0 | 0.05< | 700 | 8.0 | 10 | F |
| 2-45 | | UNIOX HC60 | 0.46 | 33 | 0.05-1.00 | 3,570 | 14.6 | 46 | P |
| 2-46 | | Vaseline | 0.00 | 55 | <0.05 | | 9.7 | 10 | F |
| 2-47 | | None | — | — | — | — | 22.7 | 60< | P |

In the absence of a blood modifying agent, the rewetting rate was 22.7% and the absorbent body migration rate was greater than 60 seconds, but the glycerin and fatty acid triesters all produced rewetting rates of not greater than 7.0% and absorbent body migration rates of not longer than 8 seconds, and therefore significantly improved the absorption performance. Of the glycerin and fatty acid triesters, however, no great improvement in absorption performance was seen with NA50 which had a melting point of above 45° C.

Similarly, the absorption performance was also significantly improved with blood modifying agents having an IOB of about 0.00-0.60, a melting point of about 45° C. or less, and a water solubility of about 0.00-0.05 g in 100 g of water at 25° C.

Example 4-2

The rewetting rate was evaluated for blood from different animals, by the procedure described above. The following blood was used for the test.
[Animal Species]
(1) Human
(2) Horse
(3) Sheep
[Types of Blood]
  Defibrinated blood: blood sampled and agitated together with glass beads in an Erlenmeyer flask for approximately 5 minutes.
  EDTA blood: 65 mL of venous blood with addition of 0.5 mL of a 12% EDTA•2K isotonic sodium chloride solution.
[Fractionation]
  Serum or blood plasma: Supernatant obtained after centrifugation of defibrinated blood or EDTA blood for 10 minutes at room temperature at about 1900 G.
  Blood cells: Obtained by removing the serum from the blood, washing twice with phosphate buffered saline (PBS), and adding phosphate buffered saline to the removed serum portion.

An absorbent article was produced in the same manner as Example 4-1, except that the tri-C2L oil fatty acid glyceride was coated at a basis weight of about 5 g/m², and the rewetting rate of each of the aforementioned blood samples was evaluated. Measurement was performed 3 times for each blood sample, and the average value was recorded.

The results are shown in Table 7 below.

TABLE 7

| | | | Rewetting rate (%) | |
|---|---|---|---|---|
| No. | Animal species | Type of blood | With blood modifying agent | Without blood modifying agent |
| 1 | Human | Defibrinated blood | 1.6 | 5.0 |
| 2 | | Defibrinated serum | 0.2 | 2.6 |
| 3 | | Defibrinated blood cells | 0.2 | 1.8 |
| 4 | | EDTA blood | 2.6 | 10.4 |
| 5 | | EDTA plasma | 0.0 | 5.8 |
| 6 | | EDTA blood cells | 0.2 | 4.3 |
| 7 | Horse | Defibrinated blood | 0.0 | 8.6 |
| 8 | | Defibrinated serum | 0.2 | 4.2 |
| 9 | | Defibrinated blood cells | 0.2 | 1.0 |
| 10 | | EDTA blood | 6.0 | 15.7 |
| 11 | | EDTA plasma | 0.1 | 9.0 |
| 12 | | EDTA blood cells | 0.1 | 1.8 |
| 13 | Sheep | Defibrinated blood | 0.2 | 5.4 |
| 14 | | Defibrinated serum | 0.3 | 1.2 |
| 15 | | Defibrinated blood cells | 0.1 | 1.1 |
| 16 | | EDTA blood | 2.9 | 8.9 |
| 17 | | EDTA plasma | 0.0 | 4.9 |
| 18 | | EDTA blood cells | 0.2 | 1.6 |

The same trend was seen with human and sheep blood as with the horse EDTA blood, as obtained in Example 4-2.

A similar trend was also observed with defibrinated blood and EDTA blood.

Example 4-3

[Evaluation of Blood Retention]
The blood retention was evaluated for a top sheet comprising a blood modifying agent and a top sheet comprising no blood modifying agent.

[Test Methods]

(1) A tri-C2L oil fatty acid glyceride was atomized on the skin contact surface of a top sheet formed from an air-through nonwoven fabric (composite fiber composed of polyester and polyethylene terephthalate, basis weight: 35 g/m$^2$), using a control seam HMA gun, for coating to a basis weight of about 5 g/m$^2$. For comparison, there was also prepared a sheet without coating with the tri-C2L oil fatty acid glyceride. Next, both the tri-C2L oil fatty acid glyceride-coated top sheet and the non-coated top sheet were cut to a size of 0.2 g, and the mass: a (g) of the cell strainer+top sheet was precisely measured.

(2) After adding about 2 mL of horse EDTA blood from the skin contact surface side, it was allowed to stand for 1 minute.

(3) The cell strainer was set in a centrifuge tube, and subjected to spin-down to remove the excess horse EDTA blood.

(4) The mass: b (g) of the top sheet containing the cell strainer+horse EDTA blood was measured.

(5) The initial absorption (g) per 1 g of top sheet was calculated by the following formula.

Initial absorption (g)=[$b$(g)−$a$(g)]/0.2(g)

(6) The cell strainer was again set in the centrifuge tube and centrifuged at room temperature for 1 minute at approximately 1,200 G.

(7) The mass: c (g) of the top sheet containing the cell strainer+horse EDTA blood was measured.

(8) The post-test absorption (g) per 1 g of top sheet was calculated by the following formula.

Post-test absorption=[$c$(g)−$a$(g)]/0.2(g)

(9) The blood retention (%) was calculated according to the following formula.

Blood retention (mass %)=100×post-test absorption (g)/initial absorption (g)

The measurement was conducted 3 times, and the average value was recorded.

The results are shown in Table 8 below.

TABLE 8

| | Blood retention (%) | |
|---|---|---|
| | With blood modifying agent | Without blood modifying agent |
| Horse EDTA blood | 3.3 | 9.2 |

The top sheets comprising blood modifying agents had low blood retentions, suggesting that blood rapidly migrated into the absorbent body after absorption.

Example 4-4

[Viscosity of Blood Containing Blood Modifying Agent]

The viscosity of the blood modifying agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood modifying agent was 50.4 mPa·s. Thus, the horse defibrinated blood containing 2 mass % PANACET 810s clearly had an approximately 90% lower viscosity than the blood containing no blood modifying agent.

It is known that blood contains components, such as blood cells and has thixotropy, and it is believed that the blood modifying agent of this disclosure can lower blood viscosity in the low viscosity range. Lowering the blood viscosity presumably allows absorbed menstrual blood to rapidly migrate from the top sheet to the absorbent body.

Example 4-5

[Photomicrograph of Blood Modifying Agent-Containing] Blood

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood modifying agent is shown in FIG. 10($a$), and a photomicrograph of menstrual blood containing PANACET 810s is shown in FIG. 10($b$).

Figure 10:
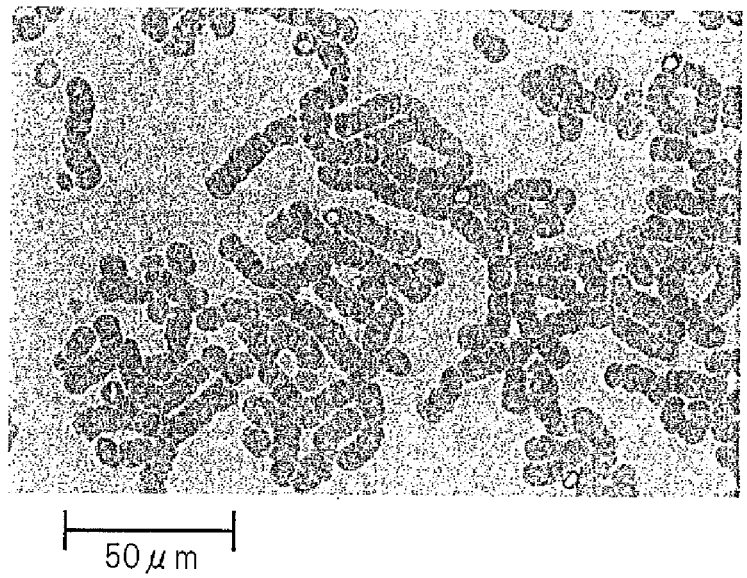
FIG. 10 is a pair of photomicrographs of menstrual blood containing and not containing a blood modifying agent.
Figure 10:
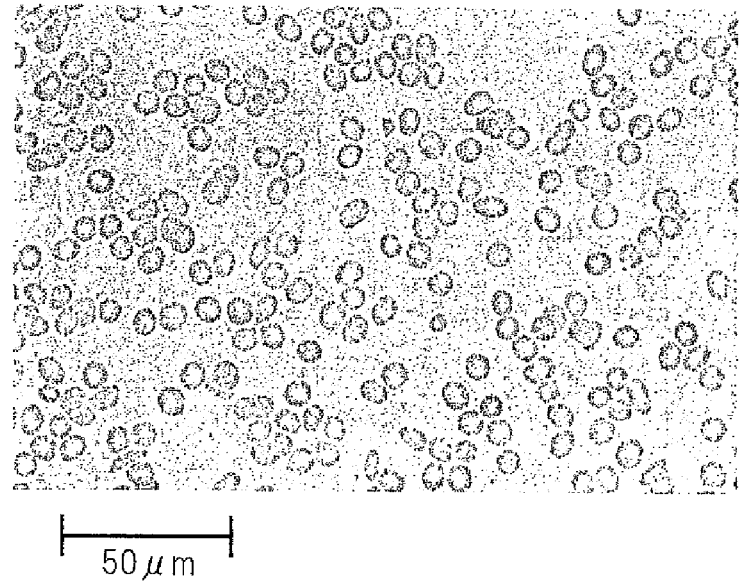

From FIG. 10 it is seen that the erythrocytes formed aggregates, such as rouleaux in the menstrual blood containing no blood modifying agent, while the erythrocytes were stably dispersed in the menstrual blood containing PANACET 810s. This suggests that the blood modifying agent functions to stabilize erythrocytes in blood.

Example 4-6

[Surface Tension of Blood Containing Blood Modifying] Agent

The surface tension of blood containing a blood modifying agent was measured by the pendant drop method, using a Drop Master500 contact angle meter by Kyowa Interface Science Co., Ltd. The surface tension was measured after adding a prescribed amount of blood modifying agent to sheep defibrinated blood, and thoroughly shaking.

Figure 11:
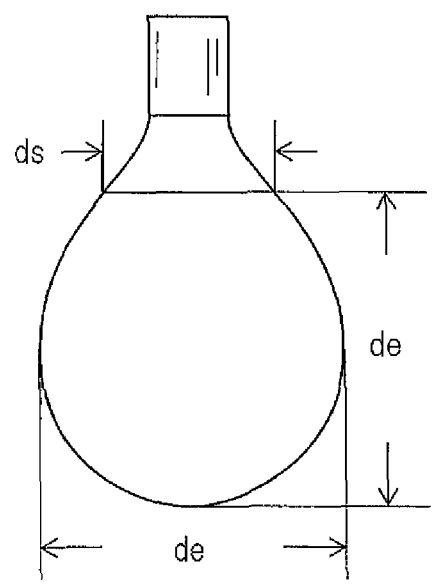
FIG. 11 is a diagram illustrating a method of measuring surface tension.

The measurement was accomplished automatically with a device, and the surface tension γ was determined by the following formula (see FIG. 11).

γ=g×ρ×($de$)$^2$×1/$H$ g: Gravitational constant

1/H: Correction factor determined from ds/de

ρ: Density de: Maximum diameter ds: Diameter at location of increase by de from dropping edge The density ρ was measured at the temperatures listed in Table 9, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 9 below.

TABLE 9

| No. | Blood modifying agent Type | Amount (mass %) | Measuring temperature (° C.) | Surface tension (mN/m) |
|---|---|---|---|---|
| 1 | — | — | 35 | 62.1 |
| 2 | PANACET 810s | 0.01 | 35 | 61.5 |
| 3 | | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Table 9 shows that the blood modifying agent can lower the surface tension of blood despite its very low solubility in water, as seen by a water solubility of about 0.00-0.05 g in 100 g of water at 25° C.

Lowering the surface tension of blood presumably allows absorbed blood to rapidly migrate from the top sheet to the absorbent body, without being retained between the top sheet fibers.

EXPLANATION OF SYMBOLS

1 Sanitary napkin (absorbent article)
2 Top sheet (liquid-permeable sheet)
3 Back sheet (liquid-impermeable sheet)
4a Absorbent body
4b Absorbent body

The invention claimed is:

1. An absorbent article comprising a liquid-permeable layer, a liquid-impermeable layer, and an absorbent body provided between the liquid-permeable layer and the liquid-impermeable layer, wherein:
the absorbent body obtained by injecting high-pressure steam onto a mixed material comprising cellulose-based water-absorbent fibers and thermoplastic resin fibers that comprise an unsaturated carboxylic acid, an unsaturated carboxylic acid anhydride or a mixture thereof as a monomer component, to increase a density of the mixed material
a mass ratio of the water-absorbent fibers to the thermoplastic resin fibers in the absorbent body is 80:20 to 50:50;
a density of the absorbent body is 0.06 to 0.14 g/cm$^3$;
a basis weight of the absorbent body is 100 to 400 g/m$^2$; and
the liquid-permeable layer comprises a blood modifying agent with an IOB of 0.00-0.60, a melting point of 45° C. or less, and a water solubility of 0.00-0.05 g in 100 g of water at 25° C.; wherein
the absorbent body has a ridge-furrow structure formed on a surface of the liquid-permeable layer side of the absorbent body and a surface of the liquid-impermeable layer side of the absorbent body; and
the ridge-furrow structure formed on the surface of the liquid-permeable layer side extends in the lengthwise direction of the absorbent article, while the ridge-furrow structure formed on the surface of the liquid-impermeable layer side extends in the widthwise direction of the absorbent article.

2. The absorbent article according to claim 1, wherein the fibers in the absorbent body are bonded together.

3. The absorbent article according to claim 1, wherein a temperature of the high-pressure steam is below a melting point of the thermoplastic resin fibers.

4. The absorbent article according to claim 1, wherein the thermoplastic resin fibers are core-sheath composite fibers having as a sheath component a modified polyolefin that has been graft-polymerized with a vinyl monomer comprising an unsaturated carboxylic acid, an unsaturated carboxylic acid anhydride or a mixture thereof, or a polymer blend of the modified polyolefin with another resin, and as a core component a resin with a higher melting point than the modified polyolefin.

5. The absorbent article according to claim 1, wherein the unsaturated carboxylic acid, unsaturated carboxylic acid anhydride or mixture thereof is maleic acid or its derivative, maleic anhydride or its derivative, or a mixture thereof.

6. The absorbent article according to claim 1, wherein a difference between a dry maximum tensile strength and a wet maximum tensile strength of the absorbent body is 1 to 5 N/25 mm.

7. The absorbent article according to claim 1, which comprises a superabsorbent material.

8. The absorbent article according to claim 1, which is colored.

9. The absorbent article according to claim 1, wherein a fiber density of the absorbent body increases from the surface of the liquid-permeable layer side toward the surface of the liquid-impermeable layer side.

10. The absorbent article according to claim 1, wherein the blood modifying agent is selected from the group consisting of following items (i)-(iii) and combinations thereof:
(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituted for a hydrogen of the hydrocarbon moiety;
with the proviso that when 2 or more oxy groups are inserted in the compound of (ii) or (iii), the oxy groups are not adjacent.

11. The absorbent article according to claim 1, wherein the blood modifying agent is selected from the group consisting of following items (i')-(iii') and combinations thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituted for a hydrogen on the hydrocarbon moiety;

with the proviso that when 2 or more same or different bonds are inserted in a compound of (ii') or (iii'), the bonds are not adjacent.

12. The absorbent article according to claim 1, wherein the blood modifying agent is selected from the group consisting of following items (A)-(F) and combinations thereof:
- (A) an ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety;
- (B) an ether of (B1) a compound having a chain hydrocarbon moiety and 2-4 hydroxyl groups substituted for hydrogens on the chain hydrocarbon moiety, and (B2) a compound having a chain hydrocarbon moiety and 1 hydroxyl group substituted for a hydrogen on the chain hydrocarbon moiety;
- (C) an ester of (C1) a carboxylic acid, hydroxy acid, alkoxy acid or oxoacid comprising a chain hydrocarbon moiety and 2-4 carboxyl groups substituted for hydrogens on the chain hydrocarbon moiety, and (C2) a compound having a chain hydrocarbon moiety and 1 hydroxyl group substituted for a hydrogen on the chain hydrocarbon moiety;
- (D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;
- (E) a polyoxy $C_2$-$C_6$ alkylene glycol, or its ester or ether; and
- (F) a chain hydrocarbon.

13. The absorbent article according to claim 1, wherein the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_2$-$C_6$ alkylene glycol, ($e_2$) an ester of a polyoxy C2-C6 alkylene glycols and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycols and a chain hydrocarbon tetracarboxylic acid, chain hydrocarbon tricarboxylic acid or chain hydrocarbon dicarboxylic acid, ($e_5$) an ether of a polyoxy $C_2$-$C_6$ alkylene glycol and a chain hydrocarbon tetraol, chain hydrocarbon triol or chain hydrocarbon diol, and ($f_1$) a chain alkane, and combinations thereof.

* * * * *